US012727879B2

(12) United States Patent
Yu

(10) Patent No.: US 12,727,879 B2
(45) Date of Patent: Sep. 8, 2026

(54) METHODS FOR LIFTING AND TIGHTENING VARIOUS AREAS OF THE BODY

(71) Applicant: Arthur Yajing Yu, La Canada Flintridge, CA (US)

(72) Inventor: Arthur Yajing Yu, La Canada Flintridge, CA (US)

( * ) Notice: Subject to any disclaimer, the term of this patent is extended or adjusted under 35 U.S.C. 154(b) by 612 days.

(21) Appl. No.: 18/121,421

(22) Filed: Mar. 14, 2023

(65) Prior Publication Data

US 2023/0355233 A1 Nov. 9, 2023

Related U.S. Application Data

(60) Provisional application No. 63/337,840, filed on May 3, 2022.

(51) Int. Cl.

| | |
|---|---|
| ***A61B 17/06*** | (2006.01) |
| *A61B 17/00* | (2006.01) |
| *A61B 18/00* | (2006.01) |

(52) U.S. Cl.

CPC .................. *A61B 17/06166* (2013.01); *A61B 2017/00792* (2013.01); *A61B 2017/06176* (2013.01); *A61B 2018/00464* (2013.01)

(58) Field of Classification Search

CPC ........... A61B 17/04; A61B 2017/0435; A61B 17/06166; A61B 2017/0432;

(Continued)

(56) References Cited

U.S. PATENT DOCUMENTS 5,013,292 A * 5/1991 Lemay .................. A61B 50/33 606/232

5,655,544 A * 8/1997 Johnson .......... A61B 17/00234 606/139

(Continued)

FOREIGN PATENT DOCUMENTS

| | | |
|---|---|---|
| EP | 3533399 A2 | 9/2019 |
| ES | 2409112 T3 | 6/2013 |

(Continued)

OTHER PUBLICATIONS

Dr. Andrew T. Cohen, Umbilicoplasty, 2016, YouTube, https://www.youtube.com/watch?v=1ynXijuhDbk&list=PLKc-TUF2iJb74RfDsTBnYN3INyiumbSyg (Year: 2016).*

(Continued)

*Primary Examiner* — Darwin P Erezo
*Assistant Examiner* — Mitchell Brian Hoag
(74) *Attorney, Agent, or Firm* — Harness Dickey & Pierce P.L.C.

(57) ABSTRACT

Methods of lifting and elevating various areas on a body including skin and tissue of a subject, such as an umbilicus region, using one or more threads including a plurality of features are provided herein. In a desired area of the body to be lifted, a method includes passing a first end of a first thread through a first path defined under the skin of the subject and passing a second end of the first thread through a second path defined under the skin of the subject and pulling one or more ends of the one or more threads in a direction to effect lifting of the desired area followed by fastening of the one or more ends of the one or more threads. The subject may have undergone liposuction prior to performance of the method.

18 Claims, 19 Drawing Sheets

(58) Field of Classification Search

CPC ...... A61B 2017/043; A61B 2017/0429; A61B 2017/0427; A61B 2017/0425; A61B 2017/0424; A61B 2017/0422; A61B 2017/042; A61B 2017/0419; A61B 2017/0414; A61B 2017/0409; A61B 2017/0417; A61B 2017/0416; A61B 2017/0412; A61B 2017/0411; A61B 2017/0404; A61B 2017/0408; A61B 2017/0406; A61B 2017/0403; A61B 17/0401; A61B 2017/0464; A61B 2017/0462; A61B 2017/0461; A61B 2017/0458; A61B 2017/0456; A61B 2017/0453; A61B 2017/0451; A61B 2017/045; A61B 2017/0448; A61B 2017/0446; A61B 2017/0445; A61B 2017/0443; A61B 2017/0441; A61B 2017/044; A61B 2017/0438; A61B 2017/0437; A61B 17/06195; A61B 2017/0619; A61B 2017/06185; A61B 2017/0618; A61B 2017/06176; A61B 2017/06171

See application file for complete search history.

(56) References Cited

U.S. PATENT DOCUMENTS

| | | | | |
|---|---|---|---|---|
| 6,848,152 | B2 | 2/2005 | Genova et al. | |
| 7,070,556 | B2 * | 7/2006 | Anderson | A61B 17/0487 112/169 |
| 8,100,940 | B2 | 1/2012 | Leung et al. | |
| 8,795,332 | B2 | 8/2014 | Leung et al. | |
| 8,876,865 | B2 | 11/2014 | Goraltchouk et al. | |
| 9,345,466 | B2 | 5/2016 | Longo et al. | |
| 9,681,941 | B2 * | 6/2017 | Griffin | A61F 2/0063 |
| 9,931,198 | B2 * | 4/2018 | Doucet | A61F 2/12 |
| 10,258,460 | B2 * | 4/2019 | Moses | A61L 31/146 |
| 11,154,393 | B2 * | 10/2021 | Limem | A61F 2/12 |
| 11,172,926 | B1 | 11/2021 | Moliver | |
| 11,413,038 | B1 * | 8/2022 | Ling | A61B 90/39 |
| 2005/0240224 | A1 | 10/2005 | Wu | |
| 2007/0239207 | A1 * | 10/2007 | Beramendi | A61B 17/06166 606/228 |
| 2009/0248071 | A1 * | 10/2009 | Saint | A61B 17/06066 606/232 |
| 2010/0137679 | A1 * | 6/2010 | Lashinski | A61B 17/0401 600/37 |
| 2012/0232339 | A1 * | 9/2012 | Csiky | A61B 1/018 604/95.04 |
| 2014/0155913 | A1 * | 6/2014 | Kim | A61B 17/0469 606/144 |
| 2023/0165668 | A1 * | 6/2023 | Einarsson | A61F 2/0045 600/30 |
| 2024/0358366 | A1 * | 10/2024 | Schanbacher | A61B 17/06166 |

FOREIGN PATENT DOCUMENTS

| | | | |
|---|---|---|---|
| ES | 2676304 | T3 | 7/2018 |
| KR | 20190131990 | A | 11/2019 |
| RU | 2724396 | C2 | 6/2020 |
| WO | WO-2009068252 | A1 | 6/2009 |

OTHER PUBLICATIONS

Office Action from Korean Application No. 10-2023-0056002 dated Mar. 11, 2025.

Hoyos, A., et al., "A Report of 736 High-Definition Lipoabdominoplasties Performed in Conjunction with Circumferential VASER Liposuction," PRS Journal, Modifications of Abdominal Lipectomy, 142(3): 662-675 (2018).

Husain, T.M., et al., "Abdominal Etching: Surgical Technique and Outcomes," PRS Journal, Plastic and Reconstructive Surgery, p. 1051-1060 (2019).

Borille, G., et al., "Prevention of Umbilical Sagging After Medium Definition Liposuction," Aesthetic Surgery Journal, 41(4): 463-473 (2021).

Kim, Y.H., et al., "Analysis of Postoperative Complications for Superficial Liposuction: A Review of 2398 Cases," PRS Journal, Plastic and Reconstructive Surgery, p. 863-871 (2011).

Bruekers, S.E., et al., "Scarless' Umbilicoplasty, A New Umbilicoplasty Technique and a Review of the English Language Literature, " Aesthetic Surgery, Annals of Plastic Surgery, 63(1): 15-20 (2009).

Hoyos, A., and Millard, J.A., "VASER-Assisted High-Definition Liposculpture," Aesthetic Surgery Journal, 27(6): 594-604 (2007).

Craig, S.B., et al., "In Search of the Ideal Female Umbilicus," Plastic and Reconstructive Surgery, 105(1): 389-392 (2000).

Lee, S.J., et al., "Computer-Aided Analysis of the 'Beautiful' Umbilicus," Aesthetic Surgery Journal, 34(5): 748-756 (2014).

Alvarez, E., et al., "Non-scarring Minimal Incision Neo-omphaloplasty in Abdominoplasty: The Alvarez Technique. A New Proposal," PRS Global Open, p. 1-12 (2021).

Paul, M.D., "Barbed Sutures in Aesthetic Plastic Surgery: Evolution of Thought and Process" Aesthetic Surgery Journal, 33(3s): 17-31 (2013).

Rohrich, R.J., et al., "Extending the Role of Liposuction in Body Contouring with Ultrasound- Assisted Liposuction," Communications in Cosmetic Surgery, p. 1090-1102 (1998).

Quinlan, F.J., "Paraffin Injections for Nasal and Other Facial Deformities, with Exhibition of a New Instrument," p. 604-608 (1902).

Parnia, R., et al., "Determining Anatomical Position of the Umbilicus in Iranian girls, and providing quantitative indices and formula to determine neo-umbilicus during abdominoplasty," Indian J Plast Surg., 45(1): 94-96 (2012).

* cited by examiner

METHODS FOR LIFTING AND TIGHTENING VARIOUS AREAS OF THE BODY

CROSS-REFERENCE TO RELATED APPLICATIONS

This application claims the benefit of U.S. Provisional Application No. 63/337,840, filed on 3 May 2022. The entire disclosure of the above application is incorporated herein by reference.

FIELD

The present disclosure relates to methods for lifting various areas of a body of a subject, such as an umbilicus, an abdominal area, a back area, a face area, a breast area, a kneecap area, and an elbow area, using one or more threads, for example, following liposuction of the area intended for lifting.

BACKGROUND

The umbilicus, or belly button, is one of the most important aesthetic focal points on the abdomen. A cosmetically attractive umbilicus is believed to be a small, vertically oriented, linear-shaped (T-shape) or oval-shaped structure. It may also have a central depression with a superior skin hood as reported in Borille et al. Borille, G. et al. (2021) *Aesthetic Surgery Journal,* 41(4):463-473. The belly button, along with the waistline, corset lines, groin lines, and curves, may all contribute to the overall body attractiveness.

FIGS. 1 and 2 provide anatomical details of a human torso region. FIG. 1 depicts a torso region of a subject showing an umbilicus 20, a waistline 30, and linea alba 40, which is located in the midline of the abdomen and formed during the embryonic stage. FIG. 2 further shows the human skeletal features of a xiphoid process 50, an iliac crest 60, and pubis symphysis 70 in the torso region. The ideal position of the umbilicus has been explored for decades by many authors and has proven to be a difficult task. Compounding the fact is that different authors use different reference points for the position of the umbilicus. Consequently, there has been much confusion among surgeons as to what can be done to improve the umbilicus position. While debate may remain as to its ideal position as discussed in Craig et al., Lee et al. and Parnia et al., it is believed that the most preferred umbilicus position is at a level near the height of the iliac crest 60 as reported in Borille et al. Craig, S. B. et al. (2000) *Plastic and reconstructive surgery,* 105(1), 389-392.; Lee, S. J. et al. (2014) *Aesthetic Surgery Journal,* 34(5):748-756; Parnia, R. et al. (2012) *Indian J Plast Surg.,* 45(1): 94-96.

Further, the ideal shape of an umbilicus presents another topic for debate. FIG. 3 shows seven different types of umbilicus shapes (Types A-G). The variations in umbilical shape were presented in Lee et al. as horizontal, round, oval, and linear. It was found that the most preferred umbilicus shapes are those of vertical orientation in an oval shape (Types A and B in FIG. 3). Unfortunately, umbilicus shape can change as a result of aging, sunbathing, weight gain, weight loss, and pregnancy, often presenting as a low lying, sad looking inverted "V" shape (e.g., Type F in FIG. 3), also referred to as a "sad umbilicus." Along with the shape change is the undesirable downward-migration of the umbilicus position, and the accompanied shortening of the lower abdomen length. This deformity can be further worsened after liposuction, due to the ensuing increased skin laxity as reported in Craig et al.

During the liposuction process, fat from the abdominal wall is removed, which can be accompanied by the descension and re-draping of the overlying skin onto a lower position, and the umbilicus position simply follows the downward migration Without a well-positioned umbilicus as a natural reference point, the appearance of the abdominal wall may become sub-optimal. Other areas of the body, such as the abdomen, the breasts, the arms, thighs, knees, elbows, and the face may also suffer from similar sagging and position and shape change thus needing correction.

Conventional surgical techniques exist for improving umbilicus position and shape, such as a tummy tuck surgery or reverse abdominoplasty. However, these conventional techniques are invasive and can result in an undesirable long incision scar and considerable time needed for recovery. Other techniques include ultrasound assisted liposuction, which has been used for more than 30 years. However, there does not appear to be any reported evidence of a successful umbilicus positional change after ultrasound assisted liposuction. Additionally, the added complications from ultrasound treatment with liposuction can include contour irregularities (12%), seromas (10%), and hyperpigmentation (2%) as reported in Hoyos et al. Hoyos, A. et al. (2018) *Plastic and Reconstructive Surgery,* 142(3):662-675. Significant blood loss leading to the necessity of blood transfusion can be an additional problem. Nonenergy-based technologies can also be used in an attempt to affect the abdominal wall aesthetics and possibly the umbilical position. One such technology is the use of polydioxanone (PDO) threads, the same as those used on the face for PDO thread lifting, as reported in Paul, M. Paul, M. (2013) *Aesthetic Surgery Journal,* 33(35):175-315. The use of PDO threads on the abdomen can be divided into two groups: 1) using non-barbed threads to insert under the skin to "promote collagen formation" and "firming" the skin; and 2) using barbed PDO threads to insert around the umbilicus to "lift" the umbilicus and the periumbilical skin. However, there does not appear to be any reported evidence showing the effectiveness of such a treatment.

For example, in the study by Borille et al., a modified Reverdain's needle was used to introduce two 3-0 nylon sutures into the upper abdomen subcutaneously in the midline from the umbilicus to the upper portion of the abdomen at a 10 cm to 15 cm distance. Afterwards, the sutures were kept in place after they were tied over the bolsters. The sutures were removed 12 days later and then the patients were followed at 2 weeks and 9 months. In the 62 female athletic body type patients, there was some increase in umbilical height (from the upper to the low edge of the umbilici, by measuring the vertical length of the umbilicus from the upper to the lower edges) for 51 patients, no change in height for 9 patients, and sagging positions for 2 patients. In Borille et al., the average height increase was 3.5 mm at two weeks, which decreased to 3 mm at the 9-month point. However, in the Borille et al. study, the demarcation of the lower edges of the umbilici could be difficult to define in most cases and liposuction can change the size and form of the umbilici to some extent. Complications were encountered in 15 patients, including skin dyschromia (9), surface irregularities (5), and ulceration (1). Although the actual changes may be difficult to visualize, Borille et al. did show that umbilical shapes and lengths could be improved, albeit on a very small scale, for example, due to the fact that the sutures were only kept in place for 12 days, at which point scarring had barely started. Therefore, tissue reattachment at a high point with the help of the 3-0 nylon sutures may not have worked as well as intended. But, if the sutures were kept longer than 12 days, more complications could be expected.

Thus, there is a need for improved methods for lifting and modifying the shape of the umbilicus, as well as other areas of the body, that avoid the need for large incisions and invasive techniques as well as considerable recovery time and provide more permanent lasting results.

SUMMARY OF THE INVENTION

This section provides a general summary of the disclosure and is not a comprehensive disclosure of its full scope or all of its features.

Provided herein are methods of lifting or elevating one or more areas of a body of a subject. In one embodiment, the method of elevating an umbilicus and/or a lower abdomen of a subject is provided. The method may include passing a first end of a first thread through a first path, passing a second end of the first thread through a second path, and pulling the first end of the first thread, and the second end of the first thread in a direction away from the upper abdominal region to elevate the umbilicus and/or the abdomen. The first path may be defined under the skin of the subject and extend from an upper abdominal region of the subject to an umbilicus region of the subject. The second path may be defined under the skin of the subject and extend from the upper abdominal region of the subject to the umbilicus region of the subject. The first thread may include a plurality of features and the first path and the second path may be separated by a first lateral distance.

In another embodiment, a method of elevating a lower abdomen of a subject is provided herein. The method includes passing a first end of a first thread through a first path and passing a second end of the first thread through a second path. The first path may be defined under the skin of the subject and extend from an upper abdominal region of the subject to the umbilicus region of the subject. The second path may be defined under the skin of the subject and extend from the upper abdominal region of the subject to an umbilicus region of the subject. The first thread may include a plurality of features as described herein. The first path and the second path may be separated by a first lateral distance. The method further includes pulling the first end of the first thread, and the second end of the first thread in a direction away from the upper abdominal region to elevate the abdomen.

In another embodiment, a method of elevating an area of a subject is provided herein. The area of the subject may be, for example, a back area, a kneecap area, an elbow area, a face area, a neck area, or a combination thereof. The method includes passing a first end of a first thread through a first path and passing a second end of the first thread through a second path. The first path may be defined under the skin of the subject and extend from an upper region of the subject to a lower region of the subject. The upper region may be an upper back region, an upper kneecap region, an upper elbow region, an upper face region, an upper neck region, or a combination thereof, and the lower region may be a lower back region, a lower kneecap region, a lower elbow region, a lower face region, a lower neck region, or a combination thereof. The second path may be defined under the skin of the subject and extend from the upper region of the subject to the lower region of the subject. The first thread includes a plurality of features as described herein. The first path and the second path are separated by a first lateral distance. The method includes pulling the first end of the first thread, and the second end of the first thread in a direction away from the upper region to elevate the area of the subject.

In another embodiment, a method of elevating a back area (e.g., upper back area, middle back area) of a subject is provided herein. The method includes passing a first end of a first thread through a first path and passing a second end of the first thread through a second path. The first path may be defined under the skin of the subject and extend from an upper back region of the subject to a lower back region of the subject. The second path may be defined under the skin of the subject and extend from the upper back region of the subject to the lower back region of the subject. The first thread may include a plurality of features as described herein. The first path and the second path may be separated by a first lateral distance. The method further includes pulling the first end of the first thread and the second end of the first thread in a direction away from the upper back region to elevate the back area.

In another embodiment, a method of elevating a kneecap area of a subject is provided herein. The method includes passing a first end of a first thread through a first path and passing a second end of the first thread through a second path. The first path may be defined under the skin of the subject and extend from an upper kneecap region of the subject to a lower kneecap region of the subject. The second path may be defined under the skin of the subject and extend from the upper kneecap region of the subject to the lower kneecap region of the subject. The first thread may include a plurality of features as described herein. The first path and the second path may be separated by a first lateral distance. The method further includes pulling the first end of the first thread, and the second end of the first thread in a direction away from the upper kneecap region to elevate the kneecap area.

In another embodiment, a method of elevating an elbow area of a subject is provided herein. The method includes passing a first end of a first thread through a first path and passing a second end of the first thread through a second path. The first path may be defined under the skin of the subject and extend from an upper elbow region of the subject to a lower elbow region of the subject. The second path may be defined under the skin of the subject and extend from the upper elbow region of the subject to the lower elbow region of the subject. The first thread may include a plurality of features as described herein. The first path and the second path may be separated by a first lateral distance. The method further includes pulling the first end of the first thread, and the second end of the first thread in a direction away from the upper elbow region to elevate the elbow area.

In another embodiment, a method of elevating a face area of a subject is provided herein. The method may be used for a facelift to lift any one of the middle cheek, lower cheek, jowl, and chin area, for example, following liposuction of those areas. The method includes passing a first end of a first thread through a first path and passing a second end of the first thread through a second path. The first path may be defined under the skin of the subject and extend from an upper face region of the subject to a lower face region of the subject. The second path may be defined under the skin of the subject and extend from the upper face region of the subject to the lower face region of the subject. The first thread may include a plurality of features as described herein. The first path and the second path may be separated by a first lateral distance. The method further includes pulling the first end of the first thread, and the second end of the first thread in a direction away from the upper face region to elevate the face area.

In another embodiment, a method of elevating a neck area of a subject is provided herein. The method includes passing a first end of a first thread through a first path and passing a second end of the first thread through a second path. The first path may be defined under the skin of the subject and extend from an upper neck region of the subject to a lower neck region of the subject. The second path may be defined under the skin of the subject and extend from the upper neck region of the subject to the lower neck region of the subject. The respective paths may have a first entry and first exit points in an area below the earlobes. The first thread may include a plurality of features as described herein. The first path and the second path may be separated by a first lateral distance. The method further includes pulling the first end of the first thread, and the second end of the first thread in a direction away from the upper neck region to elevate the neck area.

In another embodiment, a method of elevating a breast area of a subject is provided herein. The method includes passing a first end of a first thread through a first path, passing a second end of the first thread through a second path, passing a first end of a second thread through a third path, passing a second end of the second thread through a fourth path, passing a first end of a third thread through a fifth path, passing a second end of the third thread through a sixth path, passing a first end of a fourth thread through a seventh path, and passing a second end of the fourth thread through an eighth path. Each respective first, second, third, fourth, fifth, sixth, seventh, and eighth paths may be defined under the skin of the subject and extend radially from a nipple region of the subject to an upper area of the breast of the subject. Each of the first, second, third, and fourth threads may include a plurality of features as described herein. The first path and the second path maybe separated by a first lateral distance, the third path and the fourth path may be separated by a second lateral distance, the fifth path and the sixth path may be separated by a third lateral distance, and the seventh path and the eighth path may be separated by a fourth lateral distance. The method further includes pulling the respective first ends of the first thread, the second thread, the third thread, and the fourth thread, and the respective second ends of the first thread, the second thread, the third thread, and the fourth thread in a direction to elevate the breast area.

In another embodiment, another method of elevating a breast area of a subject is provided herein. The method includes passing a first end of a first thread through a first entry and through a first path, passing a first end of a second thread through the first entry and through a second path, passing a first end of a third thread through a second entry and through a third path, and passing a first end of a fourth thread through the second entry and through a fourth path. Each respective first, second, third, and fourth, paths may be defined under the skin of the subject and extend radially from a nipple region of the subject to an upper area of the breast of the subject. Each of the first, second, third, and fourth threads may include a plurality of features as described herein. The first path and the second path maybe separated by a first lateral distance and the third path and the fourth path may be separated by a second lateral distance. The method further includes pulling a second end of the first thread and a second end of the second thread both extending from the first entry and pulling a second end of the third thread and a second end of the fourth thread both extending from the second entry in a direction to elevate the breast area.

Other embodiments, including particular aspects of the embodiments summarized above, will be evident from the detailed description that follows.

BRIEF DESCRIPTION OF THE DRAWINGS

The drawings described herein are for illustrative purposes only of selected embodiments and not all possible implementations and are not intended to limit the scope of the present disclosure.

Corresponding reference numerals indicate corresponding parts throughout the several views of the drawings.

DETAILED DESCRIPTION

Figure 1:
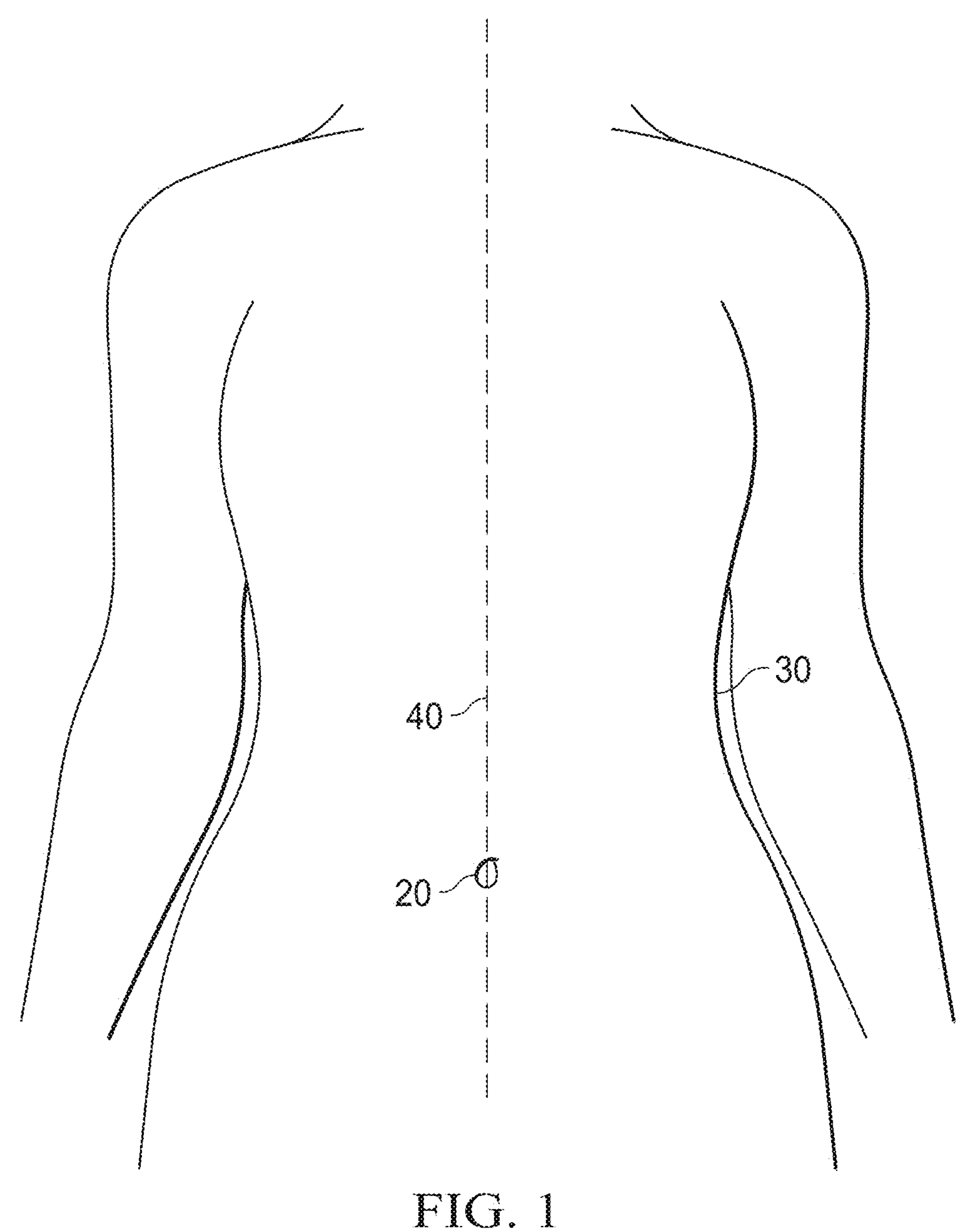
FIG. 1 illustrate a frontal view of the anatomical structure of a human torso.
Figure 2:
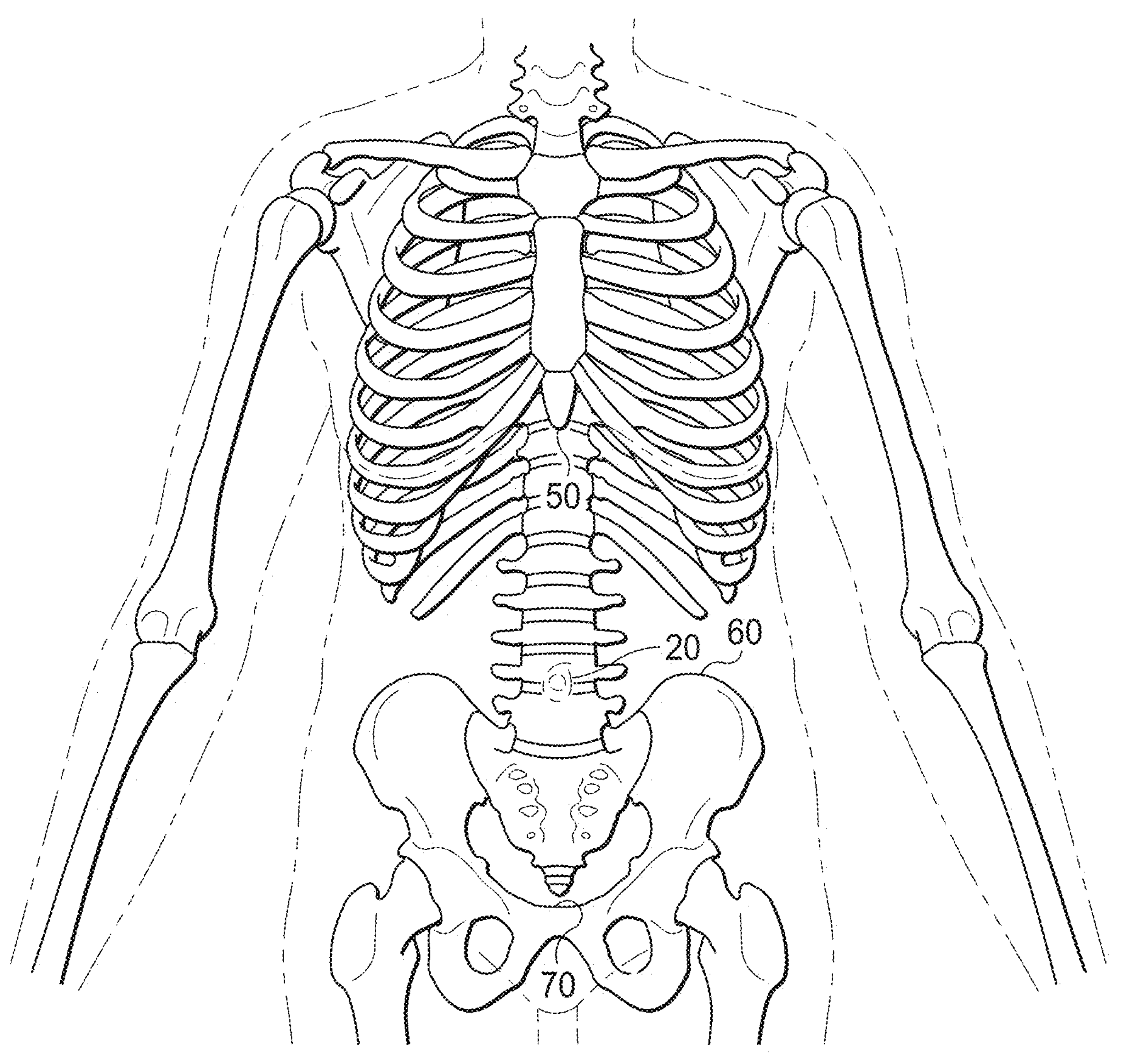
FIG. 2 illustrates a frontal view of the skeletal structure of a human torso.
Figure 3:
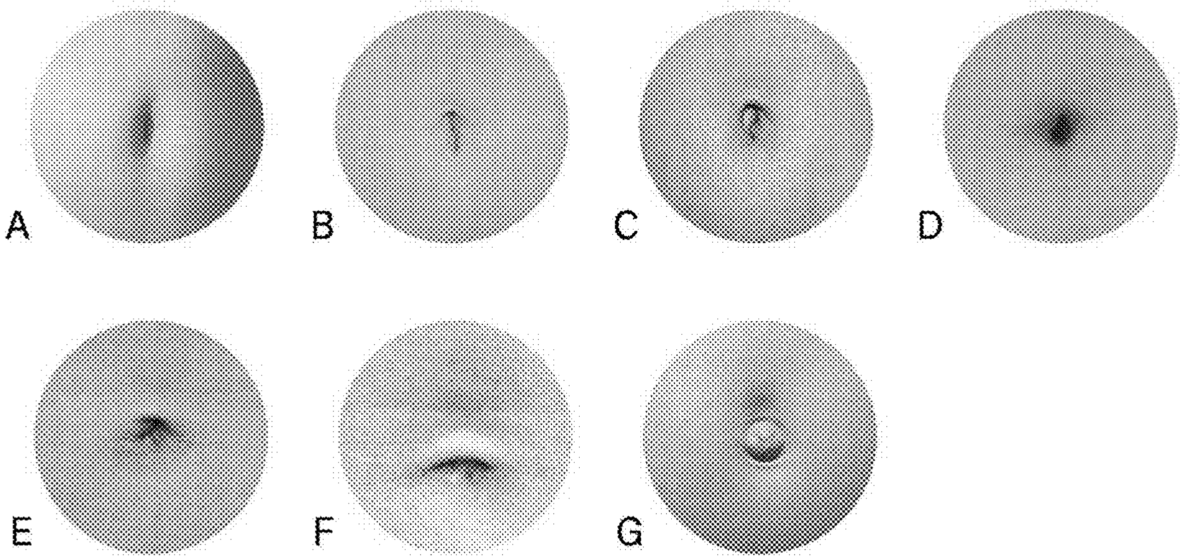
FIG. 3 shows images of different types of umbilicus shapes.

Example embodiments are provided so that this disclosure will be thorough, and will fully convey the scope to those who are skilled in the art. Numerous specific details are set forth such as examples of specific compositions, components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, elements, compositions, steps, integers, operations, and/or components, but do not preclude the presence or addition of one or more other features, integers, steps, operations, elements, components, and/or groups thereof. Although the open-ended term "comprising," is to be understood as a non-restrictive term used to describe and claim various embodiments set forth herein, in certain aspects, the term may alternatively be understood to instead be a more limiting and restrictive term, such as "consisting of" or "consisting essentially of" Thus, for any given embodiment reciting compositions, materials, components, elements, features, integers, operations, and/or process steps, the present disclosure also specifically includes embodiments consisting of, or consisting essentially of, such recited compositions, materials, components, elements, features, integers, operations, and/or process steps. In the case of "consisting of," the alternative embodiment excludes any additional compositions, materials, components, elements, features, integers, operations, and/or process steps, while in the case of "consisting essentially of," any additional compositions, materials, components, elements, features, integers, operations, and/or process steps that materially affect the basic and novel characteristics are excluded from such an embodiment, but any compositions, materials, components, elements, features, integers, operations, and/or process steps that do not materially affect the basic and novel characteristics can be included in the embodiment.

Any method steps, processes, and operations described herein are not to be construed as necessarily requiring their performance in the particular order discussed or illustrated, unless specifically identified as an order of performance. It is also to be understood that additional or alternative steps may be employed, unless otherwise indicated.

Although the terms first, second, third, etc. may be used herein to describe various steps, elements, components, regions, layers and/or sections, these steps, elements, components, regions, layers and/or sections should not be limited by these terms, unless otherwise indicated. These terms may be only used to distinguish one step, element, component, region, layer or section from another step, element, component, region, layer or section. Terms such as "first," "second," and other numerical terms when used herein do not imply a sequence or order unless clearly indicated by the context. Thus, a first step, element, component, region, layer or section discussed below could be termed a second step, element, component, region, layer or section without departing from the teachings of the example embodiments.

Spatially or temporally relative terms, such as "before," "after," "inner," "outer," "beneath," "below," "lower," "above," "upper," and the like, may be used herein for ease of description to describe one element or feature's relationship to another element(s) or feature(s) as illustrated in the figures. Spatially or temporally relative terms may be intended to encompass different orientations of the device or system in use or operation in addition to the orientation depicted in the figures.

Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. For example, "about" may comprise a variation of less than or equal to 5%, optionally less than or equal to 4%, optionally less than or equal to 3%, optionally less than or equal to 2%, optionally less than or equal to 1%, optionally less than or equal to 0.5%, and in certain aspects, optionally less than or equal to 0.1%.

In addition, disclosure of ranges includes disclosure of all values and further divided ranges within the entire range, including endpoints and sub-ranges given for the ranges.

Example embodiments will now be described more fully with reference to the accompanying drawings.

Methods for elevating and lifting various areas of a body including skin and tissue of a subject are provided herein using one or more threads. Nonlimiting examples of areas of the body, which can be lifted by performing the method described herein include an umbilicus, an abdominal area (e.g., lower abdominal area), a back area (e.g., upper back area, middle back area), a kneecap area, an elbow area, a face area, a neck area, a breast area, and combinations thereof. The methods described herein may be performed on a female subject or a male subject. Generally, in a desired area of the body to be lifted, a method may include passing a first end of a first thread through a first path defined under the skin of the subject and passing a second end of the first thread through a second path defined under the skin of the subject. The first path and the second path may be separated by a lateral distance. The method may further include pulling one or more ends of the one or more threads, for example, the first end of the first thread and the second end of the first thread in a direction to effect lifting of the desired area followed by fastening of the first end of the first thread, the second end of the first thread, or both. The one or more paths can be formed by any suitable cannula or any suitable needle both of any suitable size and length as can be determined by a person of ordinary skill in the art depending on the area targeted for lifting. For example, a 16-gauge cannula may be used. Additionally, the one or more threads (e.g., first thread, second thread, etc.) can be delivered to the path (e.g., first path, second path, etc.) by any suitable cannula or any suitable needle.

Figure 4A:
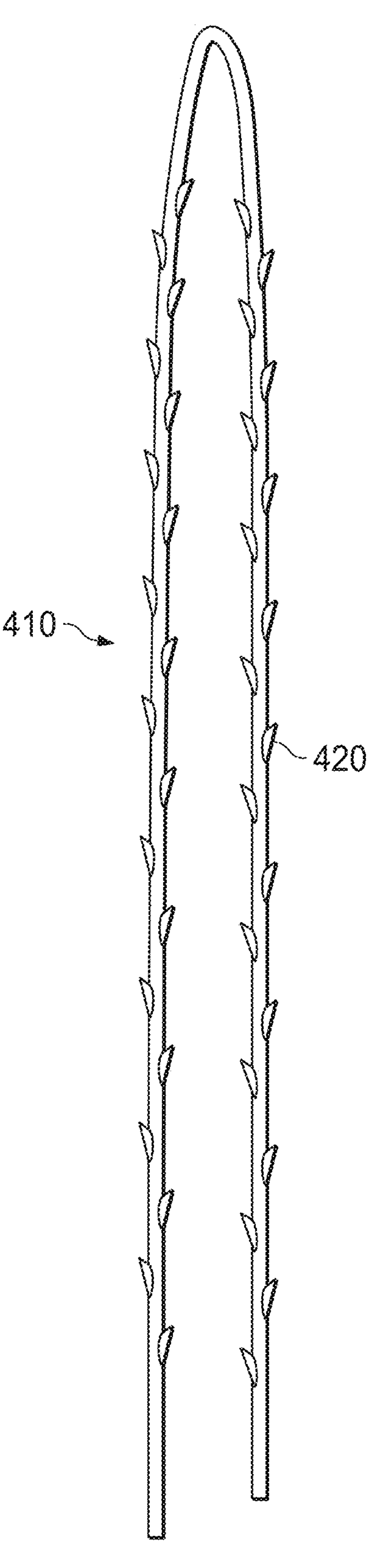
FIG. 4A illustrates a thread including a plurality of features for use in a method according to the present disclosure.
Figure 4B:
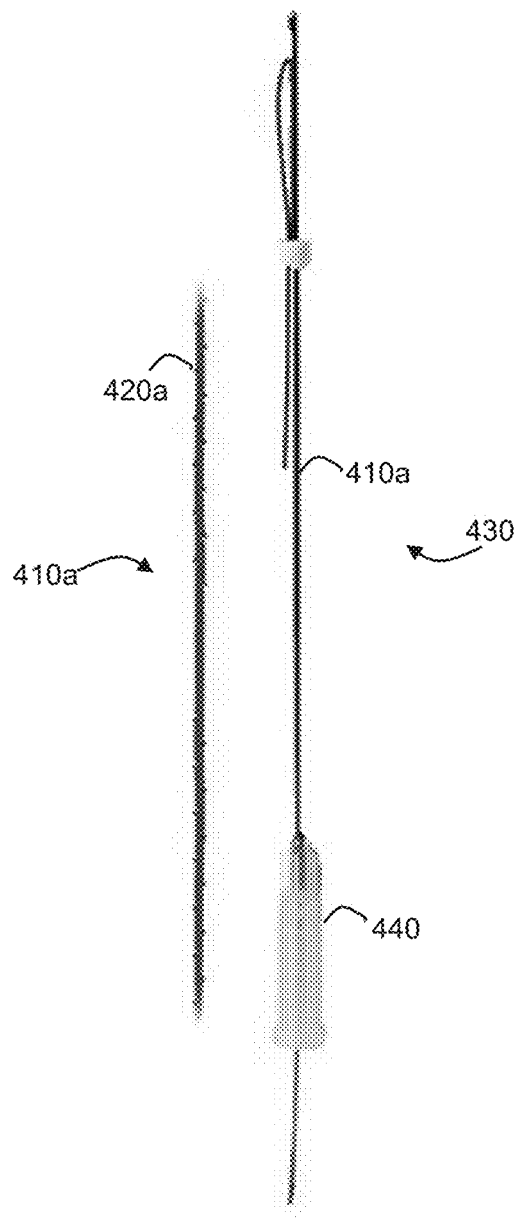
FIG. 4B illustrates another thread and thread assembly for use in a method according to the present disclosure.

In any embodiment, the one or more threads (e.g., first thread, second thread, etc.) may each independently include a plurality of features. For example, as shown in FIG. 4A, a thread 410 may include a plurality of features 420. FIG. 4B shows another example of a thread 410*a* including a plurality of features 420*a* as well as an assembly 430 including the thread 410*a* inside a cannula 440. Upon insertion of the cannula 440, with the thread 410*a*, the plurality of features 420*a* can engages with the tissue and remain in place while the cannula is retracted. The plurality of features may be one-directional, bi-directional as shown in FIG. 4A, or multi-directional. Examples of the plurality of features include, but are not limited to, barbs, knots, cones, beads, cogs, and combinations thereof. By pulling the one or more ends of the one or more threads, for example, the first end of the first thread and the second end of the first thread in a suitable direction, the plurality of features present on the threads may engage with tissue under the skin of the subject resulting in lifting of the desired area. The one or more ends of the one or more threads may be fastened, e.g., knotted or tied, or the one or more ends of the one or more threads may remain unfastened.

In any embodiment, the one or more threads (e.g., first thread, second thread, etc.) may each have a size according to the United States Pharmacopeia (USP) system of greater than or equal to about 6-0, greater than or equal to about 5-0, greater than or equal to about 4-0, greater than or equal to about 3-0, greater than or equal to about 2-0, greater than or equal to about 1-0, greater than or equal to about 0, less than or equal to about 4, less than or equal to about 3, less than or equal to about 2, or less than or equal to about 1, from about 6-0 to about 4, about 5-0 to about 4, about 3-0 to about 3, or about 2-0 to about 2. Additionally or alternatively, the one or more threads (e.g., first thread, second thread, etc.) may each have a length of greater than or equal to about 5 cm, greater than or equal to about 10 cm, greater than or equal to about 25 cm, greater than or equal to about 50 cm, less than or equal to about 150 cm, less than or equal to about 120 cm, less than or equal to about 100 cm, or less than or equal to about 75 cm; or from about 5 cm to about 150 cm, about 5 cm to about 120 cm, about 5 cm to about 100 cm, about 10 cm to about 75 cm, about 10 cm to about 50 cm, or about 10 cm to about 25 cm. It is also contemplated herein that each thread may be a unitary thread or a divided thread.

The one or more threads (e.g., first thread, second thread, etc.) may be any suitable material for use in a medical procedure, such as a mesh, a cord, a ribbon, a net, a sheet, or a combination thereof. In any embodiment, the one or more threads (e.g., first thread, second thread, etc.) may each comprise a material such as, but not limited to, polydioxanone (PDO), polycaprolactone (PCL), polyglactin, poliglecaprone, poly-L-lactic acid, polypropylene, polypropylene, nylon, silk, cotton, polyester, catgut, metal wire, collagen fiber, a tendinous material from a heterologous donor or animal, autologous tissue, and a combination thereof. For example, the thread may be a PDO thread, which can be absorbed into the tissue of the subject in about 6 to 8 months following insertion under the skin.

It is further contemplated herein that the subject had liposuction performed on the desired area prior to performing the methods described herein. For example, the liposuction may be performed in such a way that preferably only small-bored cannulas are utilized in order to preserve the vertically positioned fibers while the fat is being suctioned out. As a result, the fibrous tissue is preserved along with the neurovascular microstructures are maximally maintained. This not only helps promote a quicker recovery of the tissue after liposuction, but also makes it possible for the cogs on the PDO threads to have a firm grip on to the fibers to facilitate the accomplishment of tissue cinching, and therefore, the lifting of the umbilicus and the lower abdomen. After healing is complete, the cinched tissue is kept in a higher position and may be maintained in such a lifted position permanently. The cinched tissue can smoothen out naturally as well. For example, if lifting the umbilicus, the subject may have liposuction performed in an area between and including an upper abdominal region and an umbilicus region. Without being bound by theory, it is believed that liposuction of subcutaneous fat may create a honeycomb-like structure under the skin in the various tissue areas of interest. Thus, the plurality of features on the thread(s) can more fully engage the subcutaneous tissue under the loose skin following liposuction and achieve elevation and lifting of the relevant tissues upon pulling of the thread(s). Additionally, the tissue can heal in a higher position after the method is performed due to the use of the thread(s). Tissue healing may begin about 7 days following the procedure and may be completed about 6 months following the procedure. Furthermore, the lift or elevation achieved by performance of the method may be permanent. Advantageously, this combination of using liposuction and the methods described herein can achieve "high definition" liposuction results for patients across a wide range of body types including patients with a "sad umbilicus." Also, this combination of using liposuction and the methods described herein can eliminate the need for additional surgeries that were previously standard practice and the accompanying long incisions needed. Alternatively, it is also contemplated herein that the subject has not had liposuction performed on the desired area prior to performing the methods described herein.

Figure 5A:
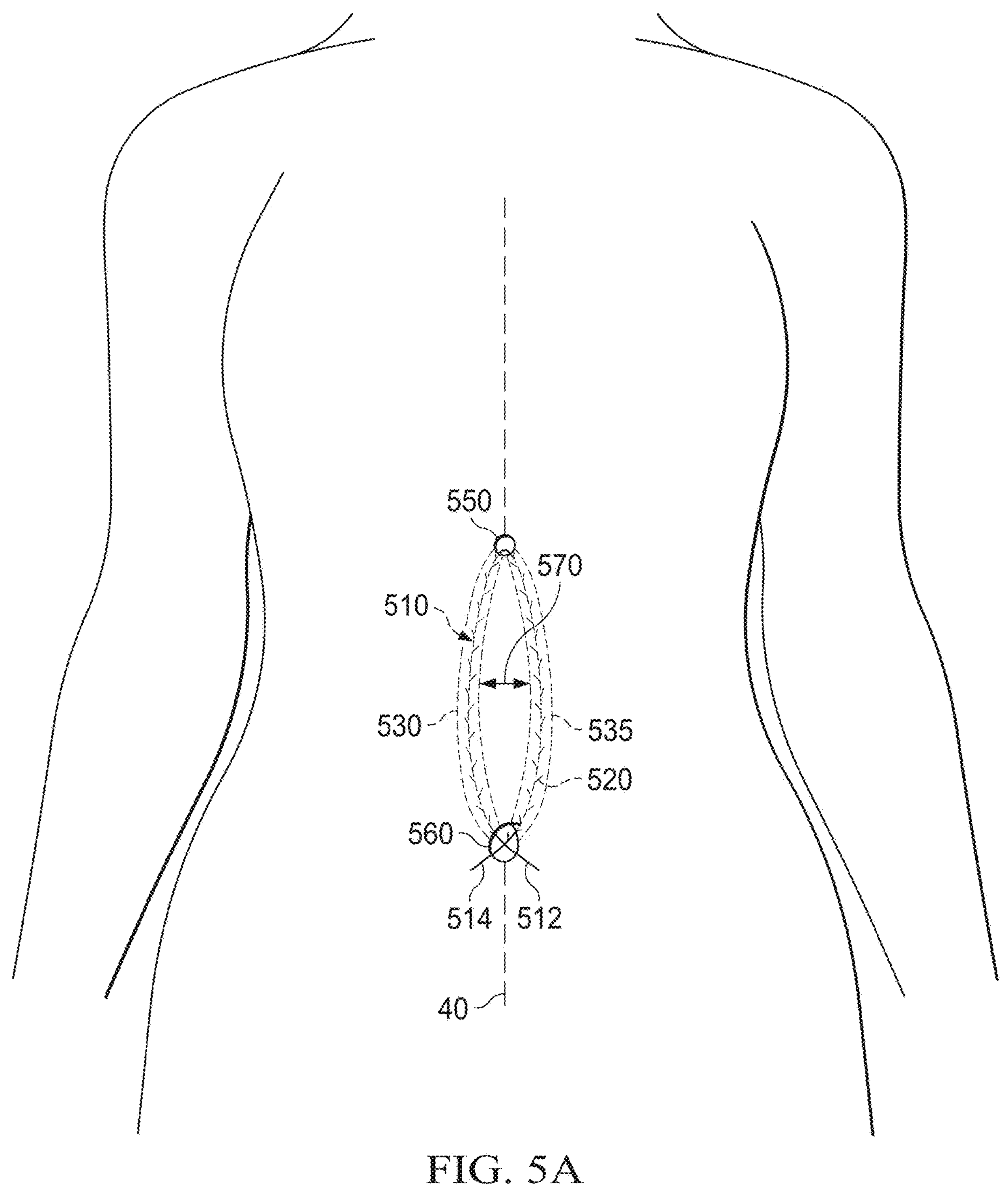
FIGS. 5A-5F illustrate an umbilical lift method according to the present disclosure.

In one embodiment, the method described herein may be a method of elevating an umbilicus of a subject. For example, as depicted in FIG. 5A, a method may include passing a first end 512 of a first thread 510 through a first path 530 and a second end 514 of the first thread 510 through a second path 535. The method further includes pulling the first end 512 of the first thread 510, and the second end 514 of the first thread 510 in a suitable direction in order to elevate the umbilicus. For example, the first end 512 and the second end 514 can be pulled in a caudal direction (e.g., away from the head of the subject in a downward and/or outward direction). In any embodiment, the first thread 510 may include a plurality of features 520 as described above. Additionally, while and/or after pulling the threads, the overlying skin tissue may be pressed to facilitate engagement of the plurality of features on the threads with the fibrous tissue so that the umbilicus is lifted and kept in the lifted position. This method may also further result in tightening and smoothing of the abdominal region (e.g., middle and lower abdomen) of the subject. Furthermore, because the umbilicus is elevated along with the middle and lower abdomen, high-definition abdominal liposuction can be achieved.

The first path 530 and the second path 535 may be defined under the skin of the subject in any suitable area between an upper abdominal region including a chest wall and the umbilicus region of the subject. For example, the first path 530 may be defined under the skin of the subject and extend from an upper abdominal region (e.g., near to or below the xiphoid process) of the subject to an umbilicus region (e.g., the umbilicus and area adjacent to the umbilicus) of the subject. Additionally, the second path 535 may be defined under the skin of the subject and extend from the upper abdominal region of the subject to the umbilicus region of the subject.

The first path 530 and the second path 535 may be separated by a first lateral distance 570 measured as the largest distance between opposing inner facing sides of the first path 530 and the second path 535. A person of ordinary skill in the art would appreciate where to place the first path 530 and the second path 535 including the length of first lateral distance 570 in order to achieve the desired result of lifting of the umbilicus such that the plurality of features 520 can engage with subcutaneous tissue of the subject so that pulling or cinching of the thread (e.g., first thread 510) results in lifting of the umbilicus. In other words, a distance between the first path 530 and the linea alba 40 of the subject and a distance between the second path 535 and the linea alba 40 of the subject can vary as needed. For example, each of the first path 530 and the second path 535 may be separated from the linea alba 40 by a distance of greater than or equal to about 1 mm, greater than or equal to about 1.5 mm, greater than or equal to about 2 mm, greater than or equal to about 2.5 mm, greater than or equal to about 3 mm, greater than or equal to about 5 mm, greater than or equal to about 10 mm, less than or equal to about 50 mm, less than or equal to about 40 mm, less than or equal to about 30 mm, less than or equal to about 20 mm; or from about 1 mm to about 50 mm, about 2 mm to about 40 mm, about 3 mm to about 30 mm, or about 5 mm to about 20 mm. Additionally or alternatively, a length of the first lateral distance 570 may be greater than or equal to about 2 mm, greater than or equal to about 3 mm, greater than or equal to about 4 mm, greater than or equal to about 5 mm, greater than or equal to about 6 mm, greater than or equal to about 10 mm, greater than or equal to about 20 mm, less than or equal to about 100 mm, less than or equal to about 80 mm, less than or equal to about 60 mm, less than or equal to about 40 mm; or from about 2 mm to about 100 mm, about 4 mm to about 80 mm, about 6 mm to about 60 mm, or about 10 mm to about 40 mm.

Figure 5B:
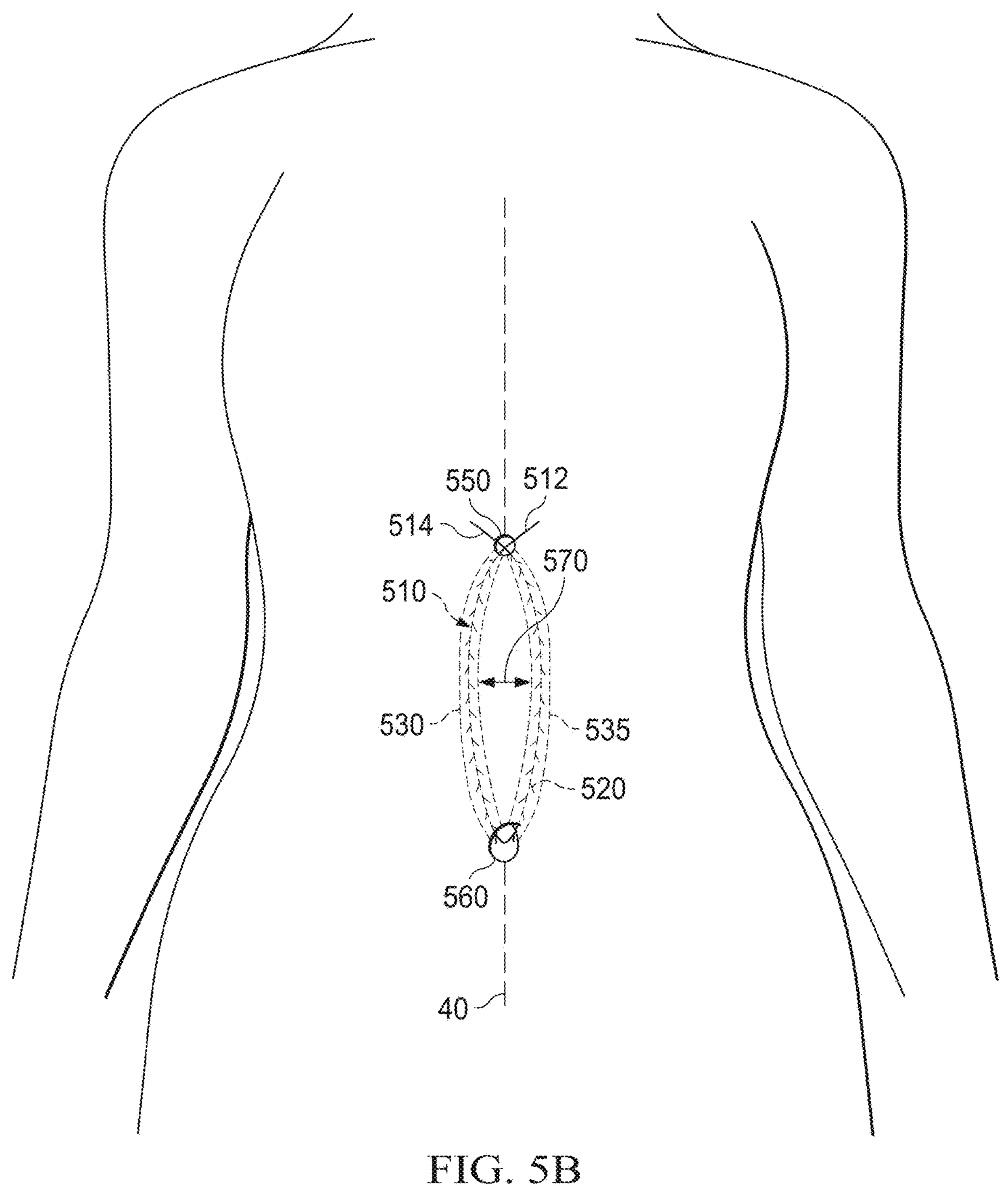
Figure 5C:
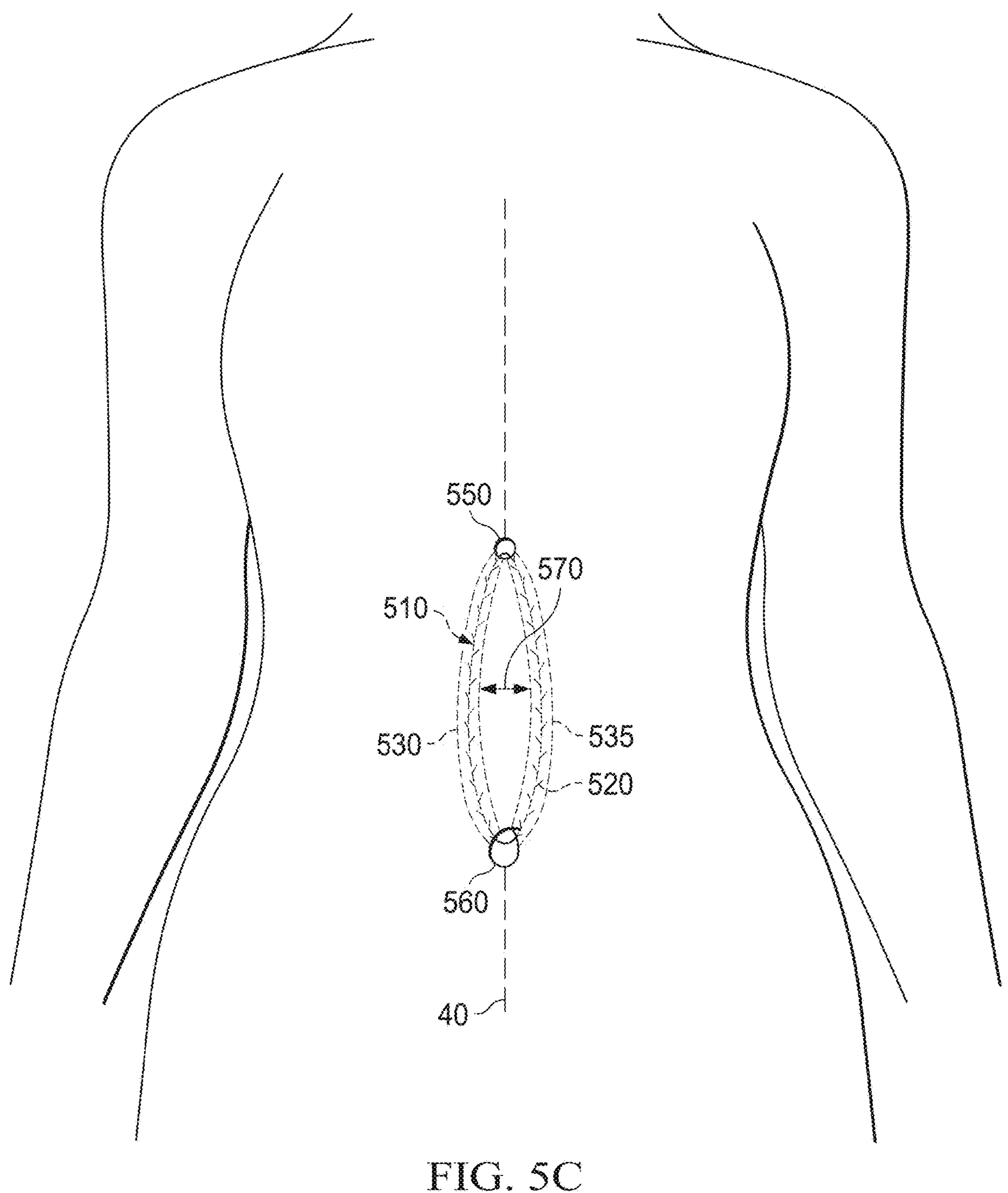

In any embodiment, the first end 512 of the first thread 510 may be introduced through a first entry 550 and pass through the first path 530 to a first exit 560, and the second end 514 of the first thread 510 may be introduced through the first entry 550 and pass through the second path 535 to the first exit 560. Alternatively, as depicted in FIG. 5B, the first end 512 of the first thread 510 may be introduced through the first exit 560 and pass through the first path 530 to the first entry 550 and the second end 514 of the first thread 510 may be introduced through the first exit 560 and passe through the second path 535 to the first entry 550. As depicted in FIG. 5C, the method may further include fastening the first end 512 of the first thread 510, the second end 514 of the first thread 510, or both by any suitable means. For example, the first end 512 and the second end 514 may be separately knotted or the first end 512 and the second end 514 may be tied together. It is contemplated herein, that upon fastening, the first end 512 and the second 514 may be tucked into and under the skin, for example, under the first entry 550 or the first exit 560. The first entry 550 and first exit 560 may then be closed, for example, with suitable sutures.

Figure 5D:
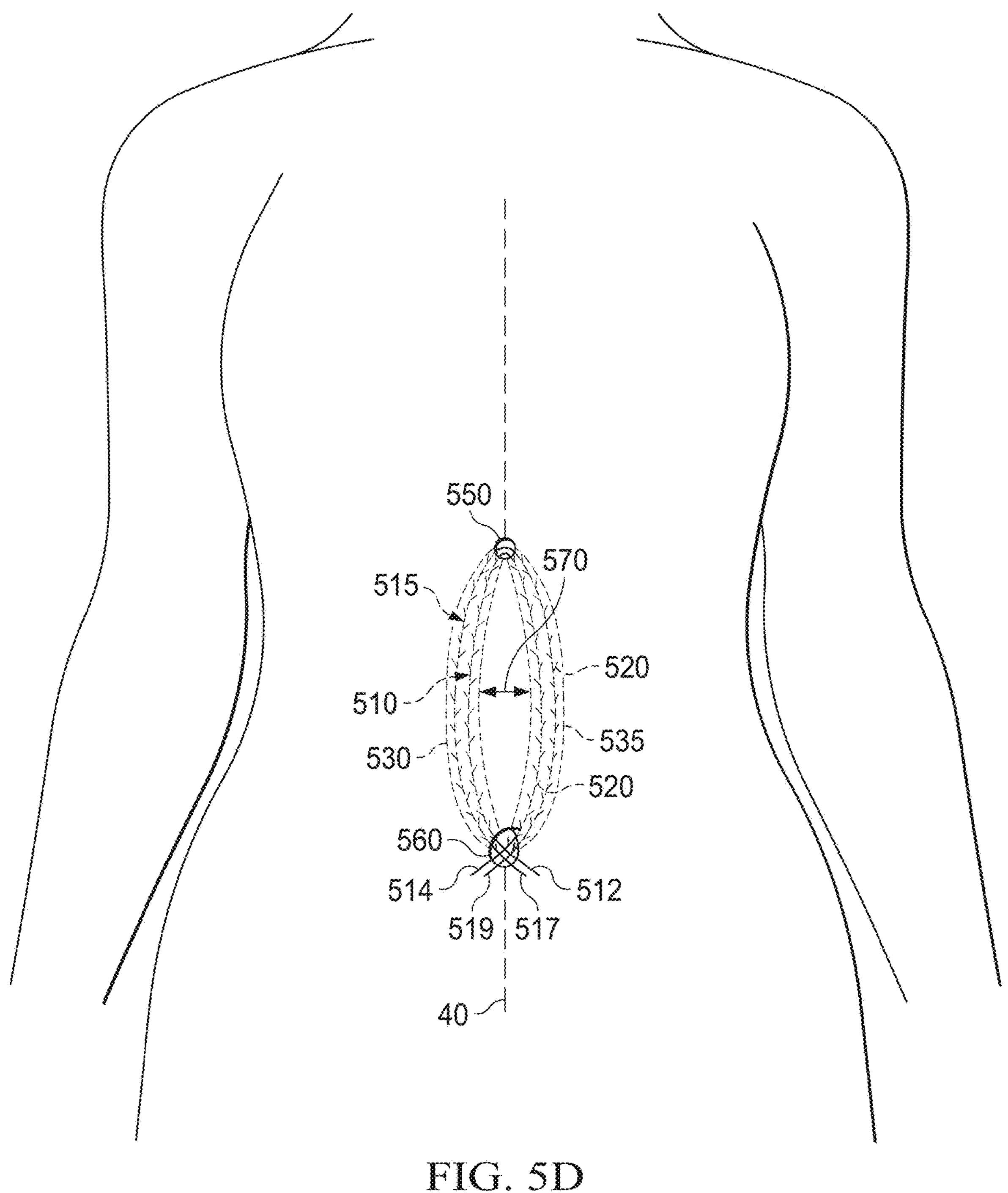

In a further embodiment, a method may include use of a second thread. For example, as illustrated in FIG. 5D, a method may further include passing a first end 517 of a second thread 515 through the first path 530 and passing a second end 519 of the second thread 515 through the second path 535. The first end 517 of the second thread 515 and the second end 519 of the second thread 515 may then be pulled in a suitable direction to elevate or lift the umbilicus. In any embodiment, the second thread 515 may include a plurality of features 520 as described above.

In any embodiment, the first end 517 of the second thread 515 may be introduced through a first entry 550 and pass through the first path 530 to a first exit 560, and the second end 519 of the second thread 515 may be introduced through the first entry 550 and pass through the second path 535 to the first exit 560. Alternatively, the first end 517 of the second thread 515 may be introduced through the first exit 560 and pass through the first path 530 to the first entry 550 and the second end 519 of the second thread 515 may be introduced through the first exit 560 and passe through the second path 535 to the first entry 550. Additionally, the method may further include fastening the first end 517 of the second thread 515, the second end 519 of the second thread 515, or both by any suitable means. For example, the first end 517 and the second end 519 may be separately knotted or the first end 517 and the second end 519 may be tied together. It is contemplated herein, that upon fastening, the first end 517 and the second 519 may be tucked into and under the skin, for example, under the first entry 550 or the first exit 560.

In a further embodiment, a method may include use three or more threads, for example, a third thread, a fourth thread, a fifth thread, etc. Each thread may include a plurality of features as described above. Thus, the method may further include passing one or more of a first end of a third thread, a first end of a fourth thread, a first end of a fifth thread, a first end of a sixth thread, a first end of a seventh thread, a first end of an eighth thread, a first end of a ninth thread, and a first end of tenth thread through the first path. Also, the method may include passing one or more of a second end of the third thread, a second end of the fourth thread, a second end of the fifth thread, a second end of the sixth thread, a second end of the seventh thread, a second end of the eighth thread, a second end of the ninth thread, and a second end of the tenth thread through the second path. If present, one or more of the first end of the third thread, the second end of the third thread, the first end of the fourth thread, the second end of the fourth thread, the first end of the fifth thread, the second end of the fifth thread, the first end of the sixth thread, the second end of the sixth thread, the first end of the seventh thread, the second end of the seventh thread, the first end of the eighth thread, the second end of the eighth thread, the first end of the ninth thread, the second end of the ninth thread, the first end of the tenth thread, and the second end of the tenth thread may be pulled in a suitable direction to elevate or lift the umbilicus. The first ends of each of the respective third through tenth threads may be introduced through a first entry (also referred to as an adit or a port) and pass through the first path to a first exit (also referred to as an adit or a port), and the second ends of each of the respective third through tenth threads may be introduced through the first entry and pass through the second path to the first exit. Alternatively, the first ends of each of the respective third through tenth threads may be introduced through the first exit and pass through the first path to the first entry and the second ends of each of the respective third through tenth threads may be introduced through the first exit and pass through the second path to the first entry. Additionally, the method may further include fastening the first ends and/or the second ends of each of the third through tenth threads by any suitable means, for example, by separately knotting each end and/or tying the ends together and they may be tucked into and under the skin, for example, under the first entry or the first exit.

Figure 5E:
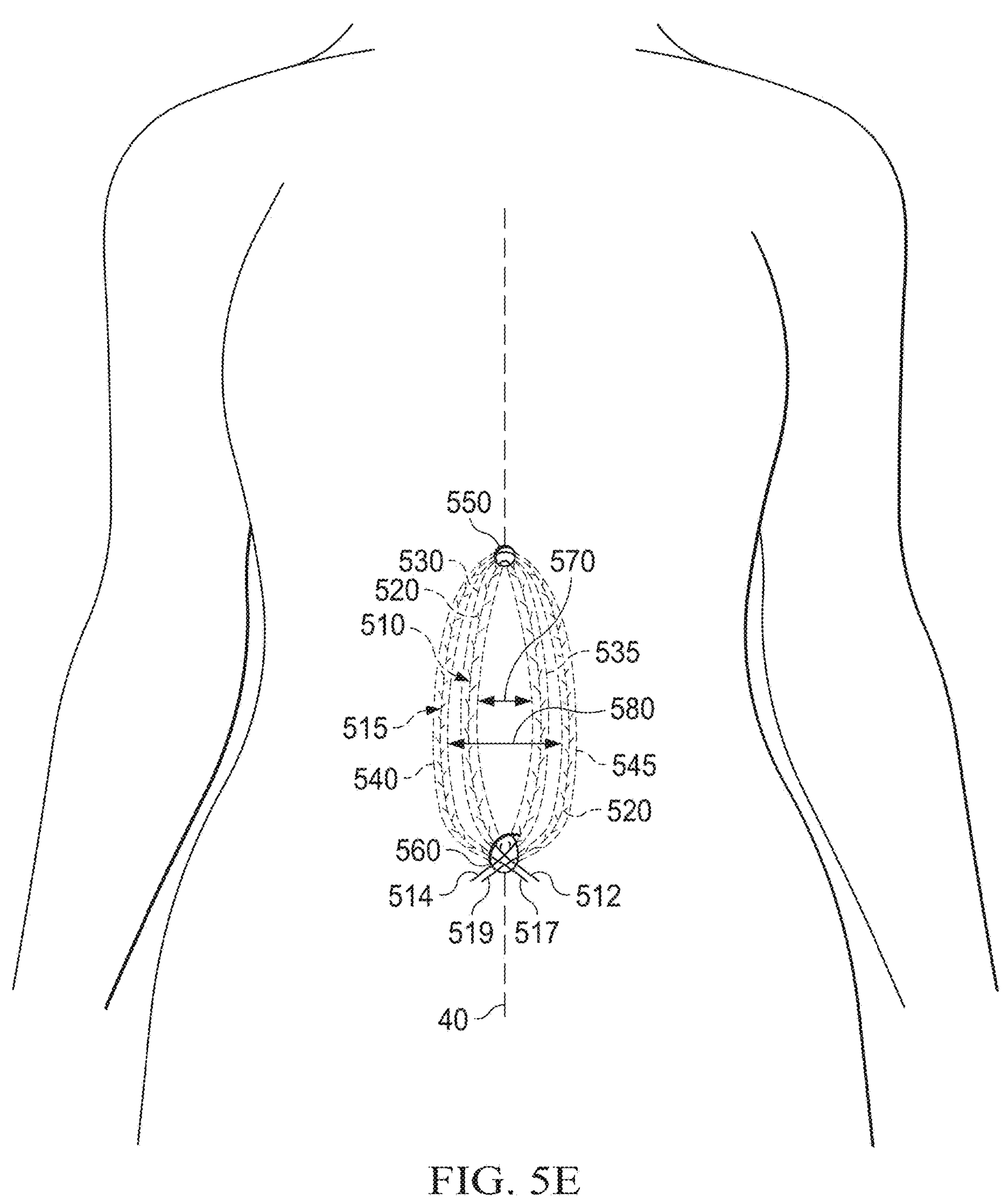

It is also contemplated herein that more than two paths may be utilized in performing the method, such as, but not limited to, a third path, a fourth path, a fifth path, a sixth path, a seventh path, an eighth path, etc., and one or more threads may pass through each path. For example, as depicted in FIG. 5E, a method may further include passing a first end 517 of a second thread 515 through a third path 540 and passing a second end 519 of the second thread 515 through a fourth path 545. The method further includes pulling the first end 517 of the second thread 515, and the second end 519 of the second thread 515 in a suitable direction in order to elevate the umbilicus.

Similar to the first path 530 and the second path 535, the third path 540 and the fourth path 545 may be defined under the skin of the subject in any suitable area between an upper abdominal region including a chest wall and the umbilicus region of the subject. For example, the third path 540 may be defined under the skin of the subject and extend from the upper abdominal region (e.g., near to or below the xiphoid process) of the subject to the umbilicus region (e.g., the umbilicus and area adjacent to the umbilicus) of the subject. The fourth path 545 may be defined under the skin of the subject and extend from the upper abdominal region of the subject to the umbilicus region of the subject.

The third path 540 and the fourth path 545 may be separated by a second lateral distance 580 measured as the largest distance between opposing inner facing sides of the third path 540 and the fourth path 545. In some embodiments, the second lateral distance 580 may be greater than the first lateral distance 570. Alternatively, the second lateral distance 580 may be less than the first lateral distance 570. A person of ordinary skill in the art would appreciate where to place the third path 540 and the fourth path 545 in relation to the first path 530 and the second path 535 including the length of the first lateral distance 570 and the length of the second lateral distance 580 in order to achieve the desired result of lifting of the umbilicus such that the plurality of features 520 can engage with subcutaneous tissue of the subject so that pulling or cinching of the thread (e.g., first thread 510, second thread 515) results in lifting of the umbilicus. In other words, a distance between the third path 540 and the linea alba 40 of the subject and a distance between the fourth path 545 and the linea alba 40 of the subject can vary as needed. For example, each of the third path 540 and the fourth path 545 may be separated from the linea alba 40 by a distance of greater than or equal to about 1 mm, greater than or equal to about 1.5 mm, greater than or equal to about 2 mm, greater than or equal to about 2.5 mm, greater than or equal to about 3 mm, greater than or equal to about 5 mm, greater than or equal to about 10 mm, less than or equal to about 50 mm, less than or equal to about 40 mm, less than or equal to about 30 mm, less than or equal to about 20 mm; or from about 1 mm to about 50 mm, about 2 mm to about 40 mm, about 3 mm to about 30 mm, or about 5 mm to about 20 mm. Additionally or alternatively, a length of the second lateral distance 580 may be greater than or equal to about 2 mm, greater than or equal to about 3 mm, greater than or equal to about 4 mm, greater than or equal to about 5 mm, greater than or equal to about 6 mm, greater than or equal to about 10 mm, greater than or equal to about 20 mm, less than or equal to about 100 mm, less than or equal to about 80 mm, less than or equal to about 60 mm, less than or equal to about 40 mm; or from about 2 mm to about 100 mm, about 4 mm to about 80 mm, about 6 mm to about 60 mm, or about 10 mm to about 40 mm.

In any embodiment, the first end 517 of the second thread 515 may be introduced through a first entry 550 and pass through the third path 540 to a first exit 560, and the second end 519 of the second thread 515 may be introduced through the first entry 550 and pass through the fourth path 545 to the first exit 560. Alternatively, the first end 517 of the second thread 515 may be introduced through the first exit 560 and pass through the second path 540 to the first entry 550 and the second end 519 of the second thread 515 may be introduced through the first exit 560 and passe through the fourth path 545 to the first entry 550. Additionally, the method may further include fastening the first end 517 of the second thread 515, the second end 519 of the second thread 515, or both by any suitable means, along with the first end 512 of the first thread 510 and/or the second end 514 of the first thread 510. For example, the first end 517 and the second end 519 may be separately knotted or the first end 517 and the second end 519 may be tied together, optionally along with the first end 512 of the first thread 510 and/or the second end 514 of the first thread 510. It is contemplated herein that upon fastening the first end 517 and the second 519 may be tucked into and under the skin, for example, under the first entry 550 or the first exit 560.

In any embodiment, a person of ordinary skill in the art recognizes that the first entry 550 and the first exit 560 may be placed as needed in order to achieve the desired lift of the umbilicus. For example, the first entry 550 may be placed in a midline of the abdomen (i.e., along the linea alba 40), or away from the midline, or any point in the upper abdomen or any point at the chest level in the chest wall. The first exit 560 may be placed in the umbilicus or in a region surrounding the umbilicus. Additionally or alternatively, the first entry 550 may positioned above the umbilicus by greater than or equal to about 1 cm, greater than or equal to about 3 cm, greater than or equal to about 5 cm, greater than or equal to about 10 cm, greater than or equal to about 15 cm, less than or equal to about 50 cm, less than or equal to about 40 cm, less than or equal to about 30 cm, or less than or equal to about 20 cm; or from about 1 cm to about 50 cm, about 1 cm to about 40 cm, about 3 cm to about 50 cm, about 3 cm to about 40 cm, about 3 cm to about 30 cm, or about 3 cm to about 20 cm.

Figure 5F:
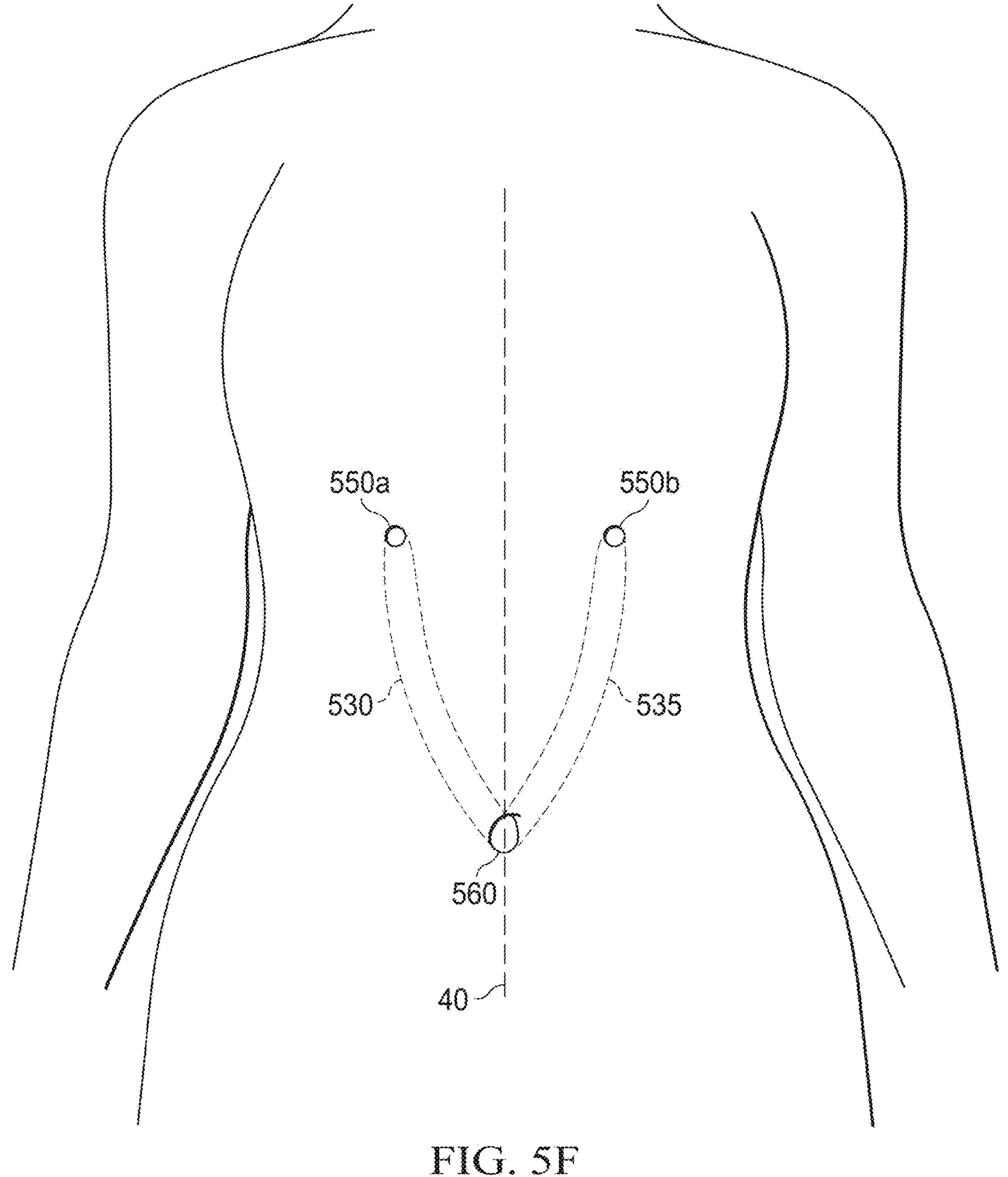

In it also contemplated herein that the first entry 550 may include a plurality of discrete entry points and/or the first exit 560 may include a plurality of discrete exit points. For example, as depicted in FIG. 5F, first entry 550*a* and first entry 550*b* may be present. The first path 530 may be defined between first entry 550*a* and first exit 560, the second path 535 may be defined between first entry 550*b* and first exit 560.

Figure 6:
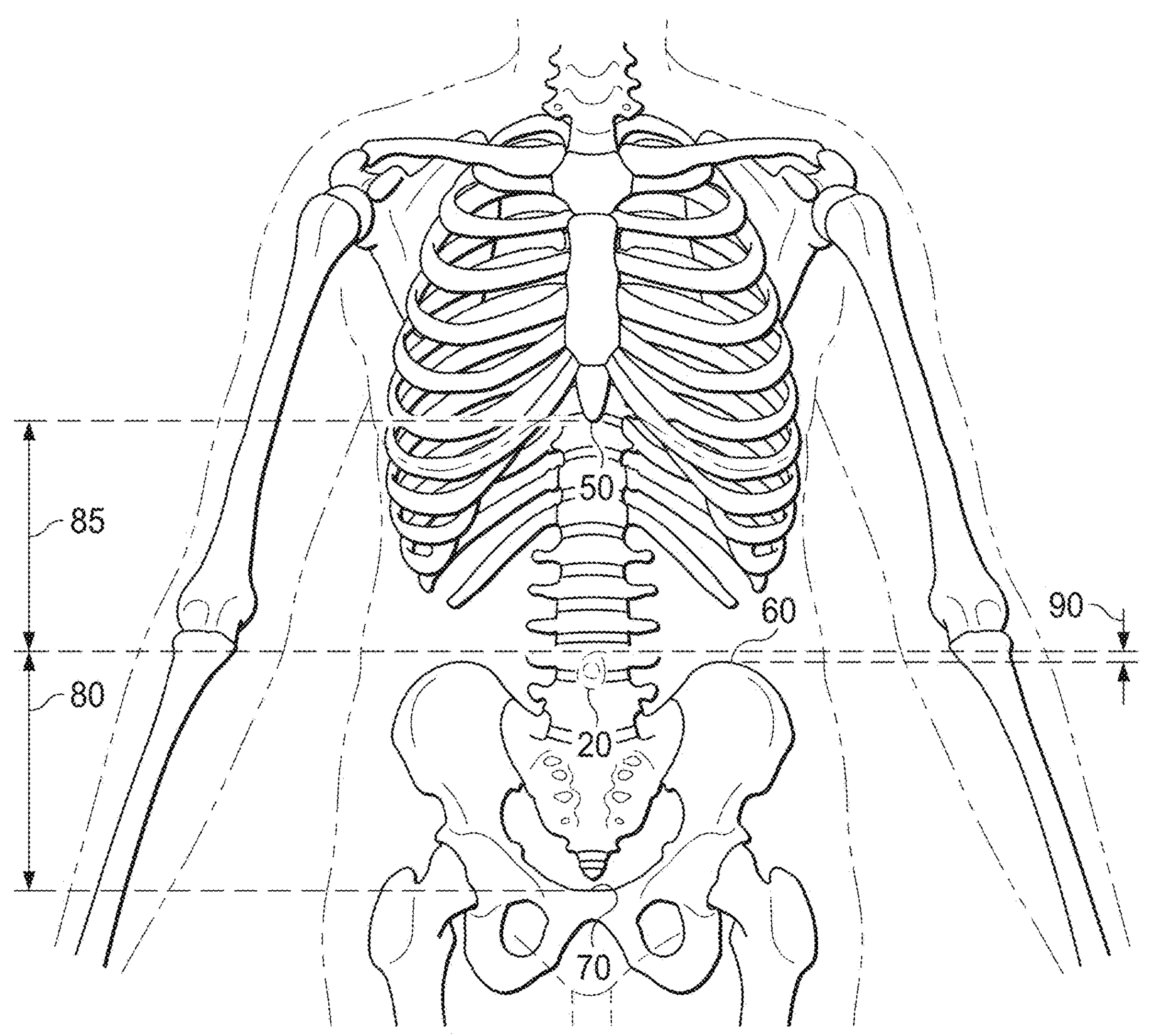
FIG. 6 illustrates areas for measurement on a frontal view of the skeletal structure of a human torso.

As stated above, by pulling the one or more ends of the one or more threads (e.g., first thread, second thread, third thread, etc.), for example, the first end of the first thread and the second end of the first thread in a suitable direction, the plurality of features present on the threads may engage with tissue under the skin of the subject resulting in lifting of the desired area. In other words, this lift or elevation of the umbilicus can be visualized as a distance between the first entry 550 and the first exit 560 becoming smaller after pulling the one or more ends of the one or more threads (e.g., first thread, second thread, third thread, etc.) than a distance between the first entry and the first exit prior to pulling. Additionally or alternatively, as illustrated in FIG. 6, this lift or elevation of the umbilicus can be quantified by measuring on the subject a distance 80 (UP distance) between an upper edge of the umbilicus 20 and the pubis symphysis 70, a distance 85 (XU distance) between xiphoid process 50 and an upper edge of the umbilicus 20, and a distance 90 (UIC) distance between an upper edge of the umbilicus 20 to an upper edge of the iliac crest 60. The UP distance, XU distance, and the UIC distance may be measured on the subject prior to performing the method and after performing the method (e.g., after pulling of the threads), for example, 3 weeks after the performance and/or 12 months after performance. After pulling the threads, one or more of the following may occur: (i) the UP distance increases; (ii) the XU distance decreases; and (iii) the UIC distance may more closely approach zero. The difference in each of the UP distance, XU distance, and UIC distance as measured prior to performing the method and measured after performing the method (e.g., measured at 12 months after performance) can be greater than or equal to about 0.25 cm, greater than or equal to about 0.5 cm, greater than or equal to about 1 cm, greater than or equal to about 1.5 cm, greater than or equal to about 2 cm, greater than or equal to about 2.5 cm, less than or equal to about 6 cm, less than or equal to about 5.5 cm, less than or equal to about 5 cm, less than or equal to about 4.5 cm, less than or equal to about 4 cm, less than or equal to about 3.5 cm, or less than or equal to about 3 cm; or from about 0.25 cm to about 6 cm, about 0.5 cm to about 5 cm, about 1 cm to about 4 cm, or about 1.5 cm to about 3.5 cm. Further, after performing the method (e.g., measured at 12 months after performance), a XU/UP ratio may be closer to 1, for example, an XU/UP ratio may be about 0.8 to about 1.1, about 0.9 to about 1.1, about 0.9 to about 1, or about 0.9.

Additionally or alternatively, an elevation of the umbilicus after performing the method (e.g., measured at 12 months after performance as the change in XU distance before and after surgery) can be greater than or equal to about 0.5 cm, greater than or equal to about 1 cm, greater than or equal to about 1.5 cm, greater than or equal to about 2 cm, greater than or equal to about 2.5 cm, greater than or equal to about 3 cm, less than or equal to about 5 cm, less than or equal to about 4.5 cm, less than or equal to about 4 cm, or less than or equal to about 3.5 cm; or from about 0.5 cm to about 5 cm, about 1 cm to about 4.5 cm or about 1.5 cm to about 4 cm.

The methods described herein may be further applied to various areas of the body of a subject wherein lifting is desired, for example, for loose skin following weight loss, liposuction, and/or aging. In any of the further embodiments, the threads may be passed in a caudal or cephalic direction and/or through a first entry or a first exit. Thus, additionally or alternatively, a method of elevating a lower abdomen of a subject is provided herein. The method includes passing a first end of a first thread through a first path and passing a second end of the first thread through a second path. The first path may be defined under the skin of the subject and extend from an upper abdominal region of the subject to the umbilicus region of the subject. The second path may be defined under the skin of the subject and extend from the upper abdominal region of the subject to an umbilicus region of the subject. The first thread may include a plurality of features as described herein. The first path and the second path may be separated by a first lateral distance. The method includes pulling the first end of the first thread, and the second end of the first thread in a direction away from the upper abdominal region to elevate the abdomen. For example, the first end and the second end can be pulled in a caudal direction (e.g., away from the head of the subject in a downward and/or outward direction). Additionally, while and/or after pulling the threads, the overlying skin tissue may be pressed to facilitate engagement of the plurality of features on the threads with the fibrous tissue so that the abdominal tissue is lifted and kept in the lifted position.

In another embodiment, a method of elevating an area of a subject is provided. The area of the subject may be, for example, a back area, a kneecap area, an elbow area, a face area, a neck area, or a combination thereof. The method may include passing a first end of a first thread through a first path and passing a second end of the first thread through a second path. The first path may be defined under the skin of the subject and extend from an upper region of the subject to a lower region of the subject. Depending on which area of the subject is undergoing the method, the upper region may be an upper back region, an upper kneecap region, an upper elbow region, an upper face region, an upper neck region, or a combination thereof, and the lower region may be a lower back region, a lower kneecap region, a lower elbow region, a lower face region, a lower neck region, or a combination thereof. The second path may be defined under the skin of the subject and extend from the upper region of the subject to the lower region of the subject. The first thread may include a plurality of features as described herein. The first path and the second path may be separated by a first lateral distance. The method includes pulling the first end of the first thread, and the second end of the first thread in a direction away from the upper region to elevate the area of the subject.

In another embodiment, a method of elevating a back area (e.g., upper back area, middle back area) of a subject is provided herein. The method includes passing a first end of a first thread through a first path and passing a second end of the first thread through a second path. The first path may be defined under the skin of the subject and extend from an upper back region of the subject to a lower back region of the subject. The second path may be defined under the skin of the subject and extend from the upper back region of the subject to the lower back region of the subject. The first thread may include a plurality of features as described herein. The first path and the second path may be separated by a first lateral distance. The method includes pulling the first end of the first thread, and the second end of the first thread in a direction away from the upper back region to elevate the back area. For example, the first end and the second end can be pulled in a cephalic direction (e.g., toward the head of the subject in an upward and/or outward direction). Additionally, while and/or after pulling the threads, the overlying skin tissue may be pressed to facilitate engagement of the plurality of features on the threads with the fibrous tissue so that the back tissue is lifted and kept in the lifted position.

In another embodiment, a method of elevating a kneecap area of a subject is provided herein. The method includes passing a first end of a first thread through a first path and passing a second end of the first thread through a second path. The first path may be defined under the skin of the subject and extend from an upper kneecap region of the subject to a lower kneecap region of the subject. The second path may be defined under the skin of the subject and extend from the upper kneecap region of the subject to the lower kneecap region of the subject. The first thread may include a plurality of features as described herein. The first path and the second path may be separated by a first lateral distance. The method includes pulling the first end of the first thread, and the second end of the first thread in a direction away from the upper kneecap region to elevate the kneecap area. For example, the first end and the second end can be pulled in a cephalic direction (e.g., toward the head of the subject in an upward and/or outward direction). Additionally, while and/or after pulling the threads, the overlying skin tissue may be pressed to facilitate engagement of the plurality of features on the threads with the fibrous tissue so that the kneecap skin and tissue are lifted and kept in the lifted position.

In another embodiment, a method of elevating an elbow area of a subject is provided herein. The method includes passing a first end of a first thread through a first path and passing a second end of the first thread through a second path. The first path may be defined under the skin of the subject and extend from an upper elbow region of the subject to a lower elbow region of the subject. The second path may be defined under the skin of the subject and extend from the upper elbow region of the subject to the lower elbow region of the subject. The first thread may include a plurality of features as described herein. The first path and the second path may be separated by a first lateral distance. The method includes pulling the first end of the first thread, and the second end of the first thread in a direction away from the upper elbow region to elevate the elbow area. For example, the first end and the second end can be pulled in a cephalic direction (e.g., toward the head of the subject in an upward and/or outward direction). Additionally, while and/or after pulling the threads, the overlying skin tissue may be pressed to facilitate engagement of the plurality of features on the threads with the fibrous tissue so that loose elbow skin and tissue are lifted and kept in the lifted position.

In another embodiment, a method of elevating a face area of a subject is provided herein. The method may be used for a facelift to lift any one of the middle cheek, lower cheek, jowl, and chin area, for example, following liposuction of those areas. The method includes passing a first end of a first thread through a first path and passing a second end of the first thread through a second path. It is contemplated that multiple threads, e.g., 4 to 16 threads, may be utilized. The first path may be defined under the skin of the subject and extend from an upper face region of the subject to a lower face region of the subject. The second path may be defined under the skin of the subject and extend from the upper face region of the subject to the lower face region of the subject. The first thread may include a plurality of features as described herein. The respective paths may have a first entry and first exit points along the hairline, in front of the hairline, in the temporal area of the face, or side cheek areas. The first path and the second path may be separated by a first lateral distance. The method includes pulling the first end of the first thread, and the second end of the first thread in a direction away from the upper face region to elevate the face area. For example, the first end and the second end can be pulled in a cephalic direction (e.g., toward the head of the subject in an upward and/or outward direction). Additionally, while and/or after pulling the threads, the overlying skin tissue may be pressed to facilitate engagement of the plurality of features on the threads with the fibrous tissue so that the facial skin and tissue are lifted and kept in the lifted position. The pulling vectors may be predetermined to serve the purpose of fully correcting any loose skin, e.g., droopy jowls and loose neck skin after liposuction.

After the method is performed, entry and exit points may be cared for with daily antibiotic ointments for about 5 days. The lower face of the subject may be supported and compressed with a post-liposuction cheek/neck garment with strong support. The garment may be worn all day for three weeks. After three weeks, the garment may be worn for about 8 to 16 hours a day. The number of threads used is usually from 4 to 12, depending on the patient's condition and the areas treated. After a about 3 months following the procedure, the results may be considered permanent.

In another embodiment, a method of elevating a neck area of a subject is provided herein. The method includes passing a first end of a first thread through a first path and passing a second end of the first thread through a second path. The first path may be defined under the skin of the subject and extend from an upper neck region of the subject to a lower neck region of the subject. The second path may be defined under the skin of the subject and extend from the upper neck region of the subject to the lower neck region of the subject. The respective paths may have a first entry and first exit points in an area below the earlobes. The first thread may include a plurality of features as described herein. The first path and the second path may be separated by a first lateral distance. The method includes pulling the first end of the first thread, and the second end of the first thread in a direction away from the upper neck region to elevate the neck area. For example, the first end and the second end can be pulled in a direction from the center of the neck toward the earlobes of the subject. Additionally, while and/or after pulling the threads, the overlying skin tissue may be pressed to facilitate engagement of the plurality of features on the threads with the fibrous tissue so that the neck skin and tissue are lifted and kept in the lifted position. The threads may be knotted and buried under the skin near the entry points.

In another embodiment, a method of elevating a breast area of a subject is provided herein. The method may include passing a first end of a first thread through a first path, passing a second end of the first thread through a second path, passing a first end of a second thread through a third path, passing a second end of the second thread through a fourth path, passing a first end of a third thread through a fifth path, passing a second end of the third thread through a sixth path, passing a first end of a fourth thread through a seventh path, and passing a second end of the fourth thread through an eighth path. Each respective first, second, third, fourth, fifth, sixth, seventh, and eighth paths may be defined under the skin of the subject and extend radially from a nipple region of the subject to an upper area of the breast of the subject. The nipple region may encompass the subject's nipple as well as the areola. The upper area of the breast may encompass upper pole(s) of the breast. Each of the first, second, third, fourth, fifth, sixth, seventh, and eighth paths may be defined between an entry (e.g., in a nipple region) and an exit (e.g., in an upper area of the breast), which may be the same or different entries and exits. For example, each of the first, second, third, and fourth paths may be defined between a first entry and a first exit, and each of the fifth, sixth, seventh, and eighth paths may be defined between a second entry and a second exit. For example, the first end of the first thread may be introduced through a first entry and pass through the first path to exit a first exit, the second end of the first thread may be introduced through the first entry and pass through the second path to exit the first exit, the first end of the second thread may be introduced through the first entry and pass through the third path to exit the first exit, and the second end of the second thread may be introduced through the first entry and pass through the fourth path to exit the first exit. Additionally or alternatively, the first end of the third thread may be introduced through a second entry and pass through the fifth path to exit a second exit, the second end of the third thread may be introduced through the second entry and pass through the sixth path to exit the second exit, the first end of the fourth thread may be introduced through the second entry and pass through the seventh path to exit the second exit, and the second end of the fourth thread may be introduced through the second entry and pass through the eighth path to exit the second exit. It is also contemplated herein that more than 4 threads may be used, such as 6 threads, 8 threads, 10 threads, 12 threads, 14 threads, 16 threads, etc. The first path and the second path maybe separated by a first lateral distance, the third path and the fourth path may be separated by a second lateral distance, the fifth path and the sixth path may be separated by a third lateral distance, and the seventh path and the eighth path may be separated by a fourth lateral distance. The method includes pulling the respective first ends of the first thread, the second thread, the third thread, and the fourth thread, and the respective second ends of the first thread, the second thread, the third thread, and the fourth thread in a suitable direction to elevate the breast area. For example, the first end and the second end of each of the threads can be pulled in a caudal direction (e.g., away from the head of the subject in a downward and/or outward direction) and/or in a direction away from the nipple region. Additionally, while and/or after pulling the threads, the overlying skin tissue may be pressed to facilitate engagement of the plurality of features on the threads with the fibrous tissue so that the nipple-areolar complex is lifted and kept in the lifted position. The threads may be knotted and buried under the skin near the entry points. The respective paths may have a first entry and first exit points in an upper, medial, or lateral aspect of the nipple region. For example, each of the threads may enter at a medial or a lateral location of the nipple region and then travel radially to the upper breast poles. Further, a person of ordinary skill in the art understands that different entry points may be chosen as needed, e.g., in the areolar region or simple in any breast area on the mid and lower poles of the breasts. Each of the first, second, third, and fourth threads may include a plurality of features as described herein. For example, the first, second, third, and fourth threads may be as depicted in FIG. 4A.

In a further embodiment, another method of elevating a breast area a subject is provided. The method may include passing a first end of a first thread through a first entry and through a first path, passing a first end of a second thread through the first entry and through a second path, passing a first end of a third thread through a second entry and through a third path, and passing a first end of a fourth thread through the second entry. Each respective first, second, third, and fourth paths may be defined under the skin of the subject and extend radially from a nipple region of the subject to an upper area of the breast of the subject. One or more of the first thread, the second thread, the third thread, and the fourth thread each comprises a plurality of features as described herein. For example, the first, second, third, and fourth threads may be as depicted in FIG. 4B. Further, the respective first ends of the first, second, third, and fourth threads may not exit the respective first, second, third, and fourth paths, but instead by embedded within the breast tissue. The first path and the second path may be separated by a first lateral distance and the third path and the fourth path may be separated by a second lateral distance. The method further includes pulling a second end of the first thread and a second end of the second thread both extending from the first entry and pulling a second end of the third thread and a second end of the fourth thread both extending from the second entry in a suitable direction to elevate the breast area. For example, the second ends of each of the threads can be pulled in a caudal direction (e.g., away from the head of the subject in a downward and/or outward direction) and/or in a direction away from the nipple region. Additionally, while and/or after pulling the threads, the overlying skin tissue may be pressed to facilitate engagement of the plurality of features on the threads with the fibrous tissue so that the nipple-areolar complex is lifted and kept in the lifted position. The threads may be knotted and buried under the skin near the entry points. The respective paths may have entry points (e.g., first entry, second entry, etc.) in an upper, medial, or lateral aspect of the nipple region. For example, each of the threads may enter at a medial or a lateral location of the nipple region and then travel radially to the upper breast poles (see FIG. 16). Further, a person of ordinary skill in the art understands that different entry points may be chosen as needed, e.g., in the areolar region or simply in any breast area on the mid and lower poles of the breasts. It is also contemplated herein that more than 4 threads may be used, such as 6 threads, 8 threads, 10 threads, 12 threads, 14 threads, 16 threads, etc. For example, if six threads are used, a first end of a fifth thread may be passed through a third entry and through a fifth path and a first end of a sixth tread may be passed through the third entry and through a sixth path. The fifth and sixth paths may each be defined under the skin of the subject and extend radially from a nipple region of the subject to an upper breast area of the subject. The fifth and sixth paths may be separated by a third lateral distance. The method may further include pulling a second end of the fifth thread and a second end of the sixth thread both extending from the third entry in a suitable direction to elevate the breast area as described above. In some embodiments, nipple and/or areola elevation can range from about 3 cm to about 8 cm or about 3 cm to about 6 cm.

If desired, lateral breast shape may be contoured by removing fat (e.g., via liposuction) from the breast tails and the harvested fat may be grafted back to the breast upper poles just under the thread insertion level to make up for a volume deficiency. After the method is performed, entry and exit points may be cared for with daily antibiotic ointments for about 5 days. The subject may also be fitted with a support garment (e.g., bra) to keep the breast upper pole skin from any down-pulling force. The support garment may be worn all day for a period of 3 months. After 3 months, the subject may only wear the bra for about 8 to 16 hours a day. After about 6 months following the procedure, the results may be considered permanent.

EXAMPLES

Example 1—Umbilical Lift and Liposuction

General Procedure

In the examples below, over a period of 36 months, 52 female patients with different body mass index (BMI) levels were studied. All patients underwent abdomen and waist liposuction and an umbilicus lift as described above. None of these patients met the criteria for abdominoplasty. The patients were measured for height and weight and the body mass index (BMI) was calculated. At a standing position, the distance from xiphoid process to the upper edge of the umbilicus (XU) and the distance from the upper edge of the umbilicus to the upper edge of the pubis symphysis (UP) were measured (see FIG. 6). The distance from the upper edge of the umbilicus to the iliac crest (UIC) level were also recorded (see FIG. 6). No effort was made to measure the actual height of the umbilicus from its upper to the lower edge, as the demarcations of the lower edge of the umbilici were not clear in many cases. The surgeries were all carried out in an ambulatory surgery center, with modest intravenous sedation. Super-wet technique was used for tumescent fluid infiltration. High-definition principles were applied (see Hoyos, A. E. et al. (2007) *Aesthet Surg J.,* 27(6):594-604) which includes the anatomical markings and the use of a power assisted liposuction (PAL, MicroAire, Chicago, IL, USA) device for corset line etching, but without the use of a VASER (Solta Medical, Bothell, WA, USA) device and without intentional etching of the "six-packs". The liposuction started with the use of a 3 mm "Mercedes" type of cannula for superficial fat removal from 5 ports (two groin ports, two infra-mammary fold ports, and one port at the upper pole of the umbilicus (behind the upper skin hood)). This was followed by liposuction of the deep fat layer below the Scarpa's fascia. During the process, a midline trough (1.5 cm in width) was created along the linea alba (see FIG. 1) above the umbilicus by removing more fat from this region. For most patients, the waistline (the narrowest point of the waist, FIG. 1) was recreated at a higher level than the patient's existing waistline position to make the lower limbs appear longer. A pinch test on the skin thickness was carried out to determine the evenness of the skin thickness and the end point of the procedure. Excessive bleeding was never encountered. The amount of fat removal typically ranged from 250 to 2000 ml, depending on the patients. Throughout the liposuction, a 3 mm Mercedes cannula was used for its ease of advancement, and less trauma to the tissues, especially the Scarpa's fascia. The integrity of the Scarpa's fascia was confirmed many times over during the lipo-abdominoplasty procedures with the same technical maneuvers.

After liposuction, a double-open-ended 16-gauge cannula (16 cm long) with a stylet was inserted through an entry point in the midline of the upper abdomen, under the skin. The entry point was made with a 16-gauge needle at about 16 cm above the umbilicus. The cannula traveled about 5 mm away from the midline (linea alba) on one side and exits the umbilicus through the port used for liposuction (to form a first path), followed by passing one end of a 43 cm long, bi-directional, 0 sized (United States Pharmacopeia, USP), barbed PDO thread (MINT 43, MINT™, Santa Fe Springs, CA, USA) (first thread) (see FIG. 4A). The other end was passed through a different path (a second path), 5 mm away from the midline on the other side of the linea alba, with the help of the cannula, using the same entry point (see FIG. 5A). The same maneuver was repeated with one more 43 cm long, bi-directional thread (second thread), via 2 laterally placed, different paths (a third path and a fourth path) (1 cm lateral to the midline on both side of the midline, FIG. 5E). The passage of the second thread was through the same entry point and the exit points were all at the apex of the umbilicus (the liposuction port). Afterwards, the ends of the first thread and the second thread on the umbilicus end were pulled with engagement of the subcutaneous tissue and the barbs on the sutures for cinching purposes. After this cinching effect was maximized, the barbed sutures were tied inside the umbilical port, and the two knots retract and become buried inside the umbilical port (see FIG. 5C). This was followed by suture-closing the umbilicus wound with one stitch using a 5-0 plain gut suture. Typically, the immediate distance between the upper edge of the umbilicus and the xyphoid process shortened from 2 cm to 8 cm. Significant upper abdominal skin bunching was seen, but no special maneuver was needed to smoothen the bunching. As this temporary "deformity" served the exact purpose of re-draping the abdominal skin onto a higher position over the abdominal musculature. No removal of the PDO sutures was necessary during the follow-up period. In the following three weeks, some "cheese wiring" occurred, however, the cinching effect remained at a significant level, as reflected by the umbilical positions in Table 1 below. The sutures typically lasted about 6 months, before becoming absorbed. During this 6-month period, the bunched skin gradually stretched out, without visible residual skin irregularity. Also noticed, immediately after the upper abdominal cinching, was the elongation of the previously shortened lower abdomen, as also stretch upward along with the uplifted umbilical stalk.

Each patient was cleaned after the surgery, followed by wound care of the open ports (only the umbilicus was closed with suturing) with a xeroform dressing. No foam pad or any other special type of pad was used for compression. Only Combine pads were used for fluid absorption. Very gentle compression was provided with a non-ribbed garment, so that the abdominal skin would have better blood circulation. After post-operation day one, an eggshell form pad at a thickness of 1.5 to 2 inches was applied on the whole abdomen with a compressing garment to facilitate the healing of the lifted tissues onto the lifted position, during the healing process for three weeks. After three weeks, a ½ inch smooth foam pad was used under a compression garment to help the patient feel more comfortable. The use of the foam and garment can be reduced to 14 to 16 hours a day. This maneuver was continued for 3 months. Afterwards, the patient was instructed to wear a lighter garment up to 6 months or longer as long as the patient can tolerate. The patients were seen post-operation day one and two to ensure the safety of the wounds. On post-operation day two, antibiotic ointment was used for wound care. A medium pressure corset was then worn by the patient for the next three months. The patients were then seen at 3-week, 3-month, and 12-month points. The XU, UP, UIC distances were measured, and the elevation of the umbilicus was determined by the change in XU distance. For skin care, the patients were instructed to apply an ample amount of oil-based body lotion twice a day to the liposuction areas.

Results

Table 1 below provides data for the 52 female patients performed on and studied over a three-year period. Two patients had a round-shaped umbilicus, three had vertical-shaped umbilici, and all the others had horizontal (reversed "V-shaped") umbilici. The patients were informed about the nature of the surgery and how the PDO thread umbilicus elevation works. Their measurements of XU, UP, and UIC distances were recorded, so were the shapes of the umbilici. After the surgery, the patients were seen at day 1, day 2, and 3 weeks post-operation. Further follow-ups were made at 3 and 12 months. Photos were taken, and measurements were made. Patients who could not comply (as many of my patients are out of state or from abroad) with the follow-up schedules are not included in the study. The umbilicus position change was calculated by measuring the upper edge of the umbilicus to the xyphoid process. Gentle pressure was applied to make sure that all the measured points were on the same plane as the xyphoid process and the pubis symphysis to ensure accuracy and consistency.

Figure 7:
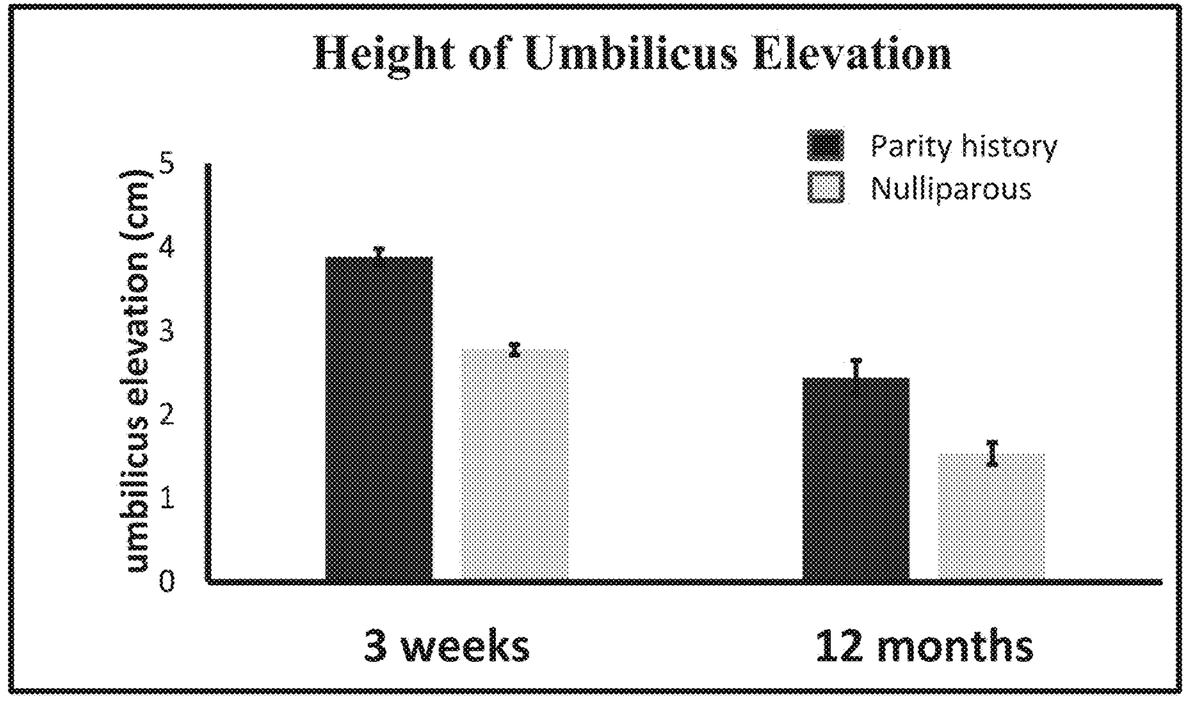
FIG. 7 is a graph providing umbilical elevation results for patients after treatment with an umbilical lift method according to the present disclosure.

Table 1 shows the data collected from the 52 included patients. Interestingly, while the range of umbilicus elevation varied, the effect was unrelated to the patients' weight, height, or the body mass index (BMI). Rather, the only significant difference was between the group of patients who had childbirth histories and the group who are nulliparous. FIG. 7 compares height of umbilicus elevation between patients with childbirth histories and nulliparous patients.

TABLE 1

| | | | | BMI | XU/UP (cm) | | | UIC (cm) | | | Shape | | Elevation (cm) | |
|---|---|---|---|---|---|---|---|---|---|---|---|---|---|---|
| Pregnancy history | Age | Ht Cm | Wt Kg | kg/ $M^2$ | Day 0 | 3 W | 12 M | day 0 | 3 W | 12 m | Day 0 | 12 m | 3 W | 12 m |
| 1, N | 26 | 168 | 52 | 18.4 | 16.8/15.2 | 14.8/17.2 | 16.0/16.0 | −0.2 | 1.8 | 0.6 | R | R | 2 | 0.8 |
| 2, N | 45 | 168 | 56 | 19.8 | 17.1/14.3 | 13.9/17.5 | 15.6/15.8 | −2.1 | 1.1 | −0.6 | H | V | 3.2 | 1.5 |
| 3, G2, P2 | 31 | 165 | 54 | 19.8 | 17.8/13.8 | 14.2/17.4 | 15.5/16.1 | −2.3 | 1.3 | 0 | H | V | 3.6 | 2.3 |
| 4, G1, P1 | 28 | 169 | 58 | 20.3 | 17.4/14.1 | 14.3/17.2 | 15.8/15.7 | −1.9 | 1.2 | −0.3 | H | V | 3.1 | 1.6 |
| 5, G1, P1 | 42 | 169 | 58 | 20.3 | 17.9/13.8 | 13.8/17.9 | 15.8/15.9 | −2.1 | 2 | 0 | H | V | 4.1 | 2.1 |
| 6, N | 29 | 168 | 58 | 20.5 | 17.3/13.2 | 13.4/17.1 | 15.1/15.4 | −3.6 | 0.3 | −1.4 | H | V | 3.9 | 2.2 |
| 7, G2, P2 | 31 | 174 | 62 | 20.5 | 21.2/13.9 | 14.7/20.4 | 17.6/17.5 | −2 | 4.5 | 1.6 | H | V | 6.5 | 3.6 |
| 8, G2, P2, | 45 | 171 | 62 | 21.2 | 20.8/13.5 | 17.5/16.8 | 18.6/15.7 | −2.5 | 0.8 | −0.3 | H | V | 3.3 | 2.2 |
| 9, N | 25 | 165 | 58 | 21.3 | 16.8/14.8 | 14.3/17.3 | 15.2/16.5 | −2.3 | 0.2 | −0.6 | H | V | 2.5 | 1.7 |
| 10, N | 31 | 165 | 58 | 21.3 | 16.5/14.5 | 13.3/17.7 | 14.6/15.6 | −1.9 | 1.3 | 0 | H | V | 3.2 | 1.9 |
| 11, G1, P1 | 35 | 166 | 59 | 21.4 | 18.4/13.1 | 13.9/16.6 | 16.5/15.0 | −2 | 1.5 | −0.1 | H | V | 3.5 | 1.9 |
| 12, G1, P1 | 33 | 175 | 66 | 21.6 | 19.9/16.2 | 16.0/18.9 | 17.0/19.1 | −3.2 | 1.3 | 0.3 | V | V | 3.9 | 2.9 |
| 13, G1, P1 | 41 | 172 | 65 | 22 | 18.5/14.3 | 14.9/17.9 | 16.0/16.8 | −2.1 | 1.5 | 0.4 | H | V | 3.6 | 2.5 |
| 14, G2, P2 | 30 | 171 | 65 | 22.2 | 18.3/13.3 | 15.2/16.5 | 16.2/15.4 | −2.3 | 0.9 | −0.2 | V | V | 3.2 | 2.1 |
| 15, N | 31 | 168 | 63 | 22.3 | 16.9/14.8 | 14.8/16.9 | 15.6/16.1 | −1.1 | 1 | 0.2 | V | V | 2.1 | 1.3 |
| 16, G2, P2 | 32 | 165 | 61 | 22.4 | 17.9/13.8 | 14.8/16.9 | 16.3/15.4 | −2.4 | 0.7 | −0.8 | H | V | 4.1 | 2.7 |
| 17, G3, P2 | 48 | 165 | 61 | 22.4 | 18.2/13.3 | 14.9/16.5 | 16.4/15.1 | −2.7 | 0.5 | −0.9 | H | H | 3.2 | 1.8 |
| 18, G2, P1 | 29 | 159 | 57 | 22.5 | 16.5/13.2 | 12.9/16.8 | 14.4/15.3 | −3.1 | 0.5 | −1 | H | V | 3.6 | 2.1 |
| 19, G1, P1 | 28 | 170 | 66 | 22.8 | 17.5/13.5 | 13.9/17.1 | 15.0/16.0 | −2.8 | 0.8 | −0.3 | H | V | 3.6 | 2.5 |
| 20, G2, P2 | 50 | 167 | 64 | 22.9 | 17.8/13.4 | 14.0/17.2 | 15.3/15.9 | −2.5 | 1.3 | 0 | H | V | 3.8 | 2.5 |
| 21, G2, P2 | 42 | 164 | 62 | 23.1 | 17.6/13.8 | 14.2/17.3 | 15.5/15.9 | −2 | 1.5 | 0.1 | H | V | 3.5 | 2.1 |
| 22, N | 29 | 164 | 62 | 23.1 | 17.0/14.1 | 14.4/16.7 | 15.5/16.6 | −1.7 | 0.9 | −0.2 | H | V | 2.6 | 1.5 |
| 23, G2, P2 | 32 | 162 | 61 | 23.2 | 17.4/12.8 | 13.6/16.6 | 15.1/15.1 | −2.8 | 1 | −0.5 | H | V | 3.8 | 2.3 |
| 24, G2, P2 | 56 | 163 | 62 | 23.3 | 17.8/13.1 | 13.5/17.4 | 15.2/15.7 | −2.5 | 1.8 | 0.1 | H | V | 4.3 | 2.6 |
| 25, N | 31 | 160 | 60 | 23.4 | 16.5/14.2 | 13.4/17.3 | 15.1/15.6 | −1.3 | 1.8 | 0.1 | H | V | 3.1 | 1.4 |
| 26, G1, P1 | 25 | 160 | 60 | 23.4 | 16.9/13.5 | 13.0/17.4 | 14.2/16.2 | −2.1 | 1.8 | −0.6 | H | V | 3.9 | 2.7 |
| 27, G1, P1 | 35 | 165 | 64 | 23.5 | 17.4/13.2 | 13.9/16.7 | 15.1/15.5 | −2.3 | 1.2 | 0 | H | V | 3.5 | 2.3 |
| 28, G2, P2 | 38 | 163 | 63 | 23.7 | 17.2/12.8 | 13.1/16.9 | 14.7/15.3 | −2 | 2.1 | 0.5 | H | V | 4.1 | 2.5 |
| 29, G2, P2 | 53 | 168 | 67 | 23.7 | 17.6/13.0 | 13.5/17.1 | 14.6/16.0 | −2.3 | 1.8 | 0.7 | H | V | 4.1 | 3 |
| 30, G2, P1 | 30 | 159 | 61 | 24.1 | 16.7/13.1 | 12.0/16.9 | 14.6/15.2 | −1.9 | 1.9 | 0.2 | H | V | 3.8 | 2.1 |
| 31, G3, P3 | 35 | 163 | 64 | 24.1 | 17.4/13.6 | 13.0/18.2 | 14.6/16.4 | −2.6 | 1.8 | 0.2 | H | V | 4.4 | 2.8 |
| 32, G2, P2 | 49 | 173 | 72 | 24.1 | 18.1/14.2 | 13.3/19.0 | 15.9/16.4 | −3.1 | 1.7 | −0.9 | H | V | 4.8 | 2.2 |
| 33, G3, P2 | 39 | 165 | 66 | 24.2 | 17.8/13.2 | 14.3/16.8 | 15.3/15.5 | −2.6 | 0.9 | −0.3 | H | V | 3.5 | 2.3 |
| 34, G1, P1 | 33 | 162 | 64 | 24.4 | 17.5/12.3 | 14.3/15.5 | 15.0/14.8 | −3.6 | −0.4 | −1.1 | R | V | 3.2 | 2.5 |
| 35, G2, P1 | 35 | 171 | 72 | 24.6 | 18.2/14.1 | 13.5/18.8 | 15.0/17.3 | −2.8 | 1.9 | 0.4 | H | V | 4.7 | 3.2 |
| 36, G2, P2 | 32 | 158 | 62 | 24.8 | 16.8/12.3 | 13.7/15.4 | 14.8/14.3 | −2.9 | 0.2 | −0.9 | H | V | 3.1 | 2 |
| 37, N | 42 | 162 | 65 | 24.8 | 16.3/14.5 | 13.9/16.9 | 14.8/16.0 | −1.1 | 1.3 | 0.4 | H | V | 2.4 | 1.5 |
| 38, G2, P1 | 35 | 171 | 72 | 25 | 18.2/13.5 | 13.7/18.0 | 16.1/15.6 | −2.5 | 2 | −0.4 | H | V | 4.5 | 2.1 |
| 39, G2, P2 | 32 | 162 | 66 | 25.1 | 17.4/13.4 | 13.6/17.2 | 15.0/16.0 | −2.3 | 1.5 | −0.1 | H | V | 3.8 | 2.4 |
| 40, G2, P2 | 38 | 166 | 71 | 25.3 | 17.8/13.2 | 13.6/17.4 | 14.9/16.1 | −2.6 | 1.6 | −0.3 | H | V | 4.2 | 2.9 |
| 41, G1, P1 | 28 | 153 | 60 | 25.6 | 17.1/12.0 | 13.6/15.5 | 14.8/14.3 | −2.5 | 1 | −0.2 | H | V | 3.5 | 2.3 |
| 42, G2, P1 | 40 | 155 | 62 | 25.8 | 16.9/13.1 | 13.1/16.9 | 14.4/15.6 | −3.1 | 0.7 | −0.6 | H | V | 3.8 | 2.5 |
| 43, G3, P3 | 38 | 166 | 71 | 25.8 | 17.6/13.9 | 13.4/18.1 | 14.7/16.8 | −2.1 | 2.1 | 0.8 | H | V | 4.2 | 2.9 |
| 44, G2, P2 | 48 | 162 | 64 | 25.9 | 17.3/13.4 | 14.1/16.6 | 15.1/16.1 | −2.4 | 0.8 | 0.3 | H | V | 3.2 | 2.7 |
| 45, G2, P2 | 35 | 180 | 84 | 25.9 | 19.3/14.5 | 14.0/19.8 | 16.2/17.6 | −3.2 | 2.1 | −0.1 | H | V | 5.3 | 3.1 |
| 46, G1, P1 | 34 | 152 | 60 | 26 | 16.2/12.8 | 13.1/15.9 | 13.9/15.1 | −2.6 | 0.5 | −0.3 | H | V | 3.1 | 2.3 |
| 47, G2, P2 | 48 | 168 | 74 | 26.2 | 17.2/14.3 | 13.0/18.5 | 14.0/17.5 | −1.2 | 3 | 1.9 | H | R | 4.2 | 3.1 |
| 48, G2, P2 | 42 | 163 | 70 | 26.3 | 17.5/13.2 | 13.2/17.5 | 15.3/15.4 | −3.1 | 1.2 | −0.9 | H | V | 4.3 | 2.2 |
| 49, G2, P1 | 48 | 166 | 74 | 26.9 | 17.7/13.1 | 13.8/17.0 | 15.4/15.4 | −2.9 | 1 | −0.6 | H | V | 3.9 | 2.3 |
| 50, G3, P3 | 49 | 158 | 68 | 27.2 | 16.2/13.8 | 12.5/17.5 | 13.6/16.4 | −0.8 | 2.9 | 1.8 | H | V | 3.7 | 2.6 |
| 51, G2, P2 | 42 | 157 | 70 | 28.4 | 16.4/13.3 | 12.7/17.0 | 14.4/15.3 | −2.1 | 1.6 | −0.1 | H | H | 3.7 | 2 |
| 52, G2, P2 | 38 | 154 | 75 | 31.6 | 16.5/11.6 | 12.6/15.5 | 14.2/13.9 | −1.9 | 2 | 0.4 | H | V | 3.9 | 2.3 |
| mean | 36.9 | 165 | 64 | 23.6 | 17.6/13.6 | 13.9/17.2 | 15.3/15.6 | −2.3 | 1.4 | −0.1 | | | 3.7 | 2.3 |

Abbreviations: G1: one pregnancy; G2: 2 pregnancies; G3: 3 pregnancies P1: one birth; P2: 2 births; P3: 3 births; N: nulliparous, no birth; Ht: height; Wt: weight; BMI: body mass index; R: round umbilicus shape; V: vertical umbilicus shape; H: horizontal umbilicus shape; B/A ratio: the XU/UP ratio before and after surgery; w: week; and m: month.

No infection was seen in the patients. The sutures were all absorbed in the patients when seen at 12 months. One patient had some pain (rated 2-3 on a scale of 0 to 10) in the midline abdomen whenever she tried to get out of bed in the first 2 months. But she never required any pain medication. Twelve patients reported soreness in the upper midline abdomen (rated 1, on a scale of 0-10). Initial upper abdominal bunching was seen in all patients immediately after surgery, but only 24 out of the 52 patients showed some skin bunching at 3-week follow-ups. None of the bunching remained at the 12-month follow-up visit. The scar at the apex of the umbilicus appeared to be the same as any other patient who underwent abdominal liposuction without the umbilical elevation procedure. Thirty-three patients had pin-point skin discoloration at the 16G needle entry point, and in 21 of these patients, this light black spot was still visible by three months. However, at the 12-month follow-up, all but 4 of these pin-point skin pigmentation problems disappeared, and the 4 patients who had the pin-point skin discoloration confirmed that the discoloration was faint and barely visible.

A patient satisfaction survey was done, with ratings stratified as "bad, fair, good, and perfect". The patient satisfaction rate was high at 100% (good or perfect), and this was reflected by the patients' verbal expression at the time of their follow-up visits, even at the 12-month point. Scoring of the liposuction results by 12 volunteers, made up of regular patients who were scheduled for liposuction procedures, were performed. Before and after (12 months) photos of 10 consecutive patients without the umbilical elevation (Group 1) and 10 consecutive patients with the umbilical elevation procedure (Group 2) were presented to the patients with a blinded approach. The photos of the patients in Group 2 consistently won higher scores (from a scale of 0 to 10, 8.91 points) vs. the photos of Group 1 patients (5.83 points). The difference between the scores was statistically significant ($p<0.001$). The most important factor influencing the volunteers' judgement on the results was the shape changes of the umbilici. Interestingly, while many participants were not able to recognize the higher locations of the umbilici in the Group 2 patients, most did detect the flatter lower and periumbilical abdomen in Group 2.

Figure 8A:
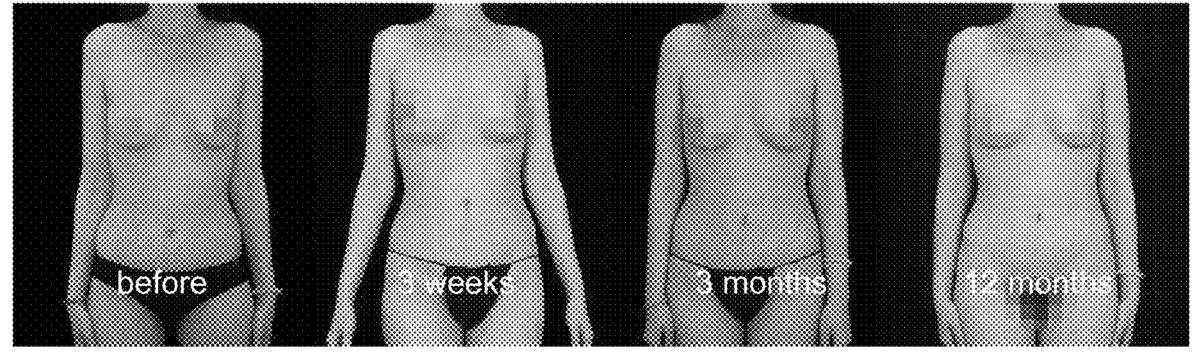
FIGS. 8A and 8B are images of a patient before and after treatment with an umbilical lift method according to the present disclosure.
Figure 8B:
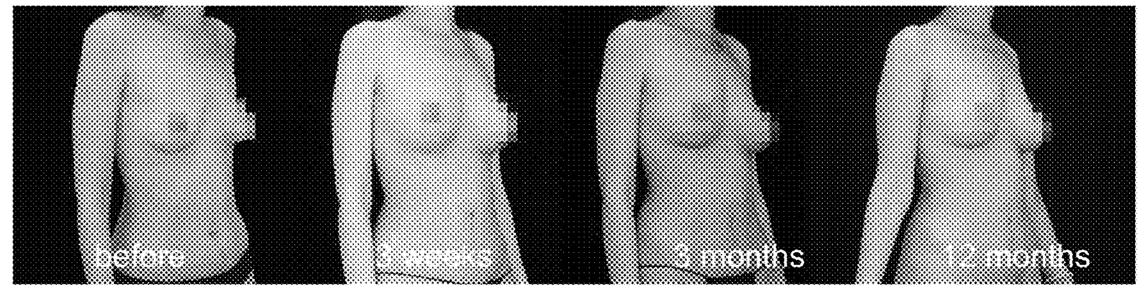

Images of patients from the study with different physical builds are shown in FIGS. 8A to 11B. FIGS. 8A and 8B show images of one patient studied, a 31-year-old female, before the procedure including liposuction and umbilicus lift, 3 weeks after the procedure, 3 months after the procedure and 12 months after the procedure. The patient had the following measurements: height of 174 cm, weight of 62 kg, BMI 20.5, G2, P2. The patient underwent liposuction of the abdomen and waist. A total of 750 ml of fat was removed and 300 ml of purified fat was grafted to each breast. The umbilicus elevation procedure was done at the same time. The shape of the umbilicus changed from horizontal to vertical. The XU/UP was 21.2/13.9 cm before the procedure 14.7/20.4 cm at 3 weeks, and 16.5/15 cm at 12 months after the procedure. The upper edge of the umbilicus was 2 cm below iliac crests (IC) before the procedure, 4.5 cm above the IC at 3 weeks and 1.6 cm above the IC at 12 months. The elevation of the umbilicus was 6.5 cm at 3 weeks, and 3.6 cm at 12 months. The lower abdomen and the periumbilical area became much smoother, without any lumpiness. This patient had umbilical piercing, which explains the temporary extra-depression just above the upper edge of the umbilicus at the 3-week follow-up.

Figure 9A:
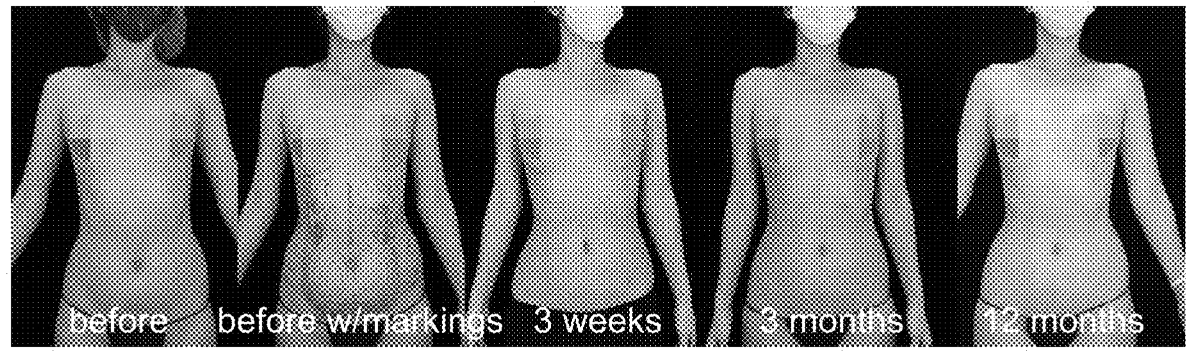
FIGS. 9A and 9B are images of a patient before and after treatment with an umbilical lift method according to the present disclosure.
Figure 9B:
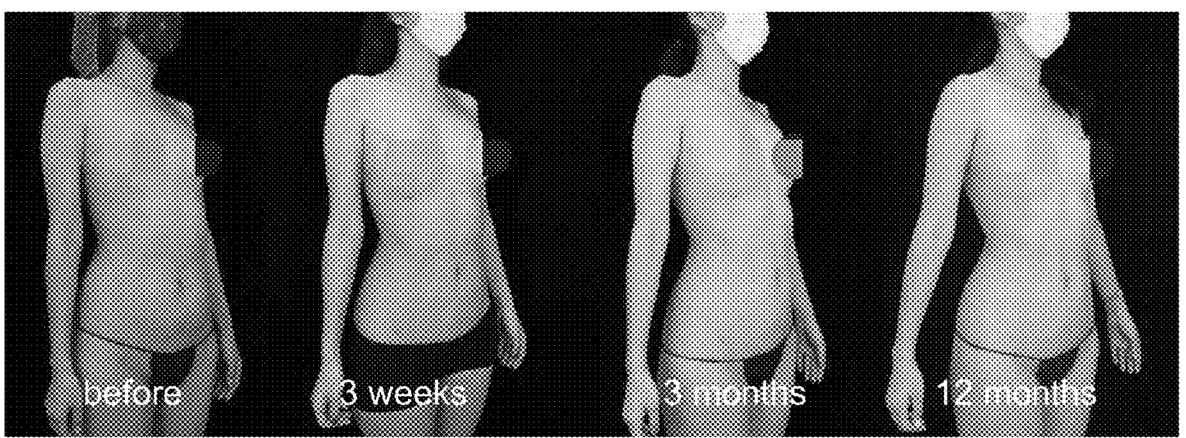

FIGS. 9A and 9B show images of another patient studied, a 33-year-old female, before the procedure including liposuction and umbilicus lift, 3 weeks after the procedure, 3 months after the procedure and 12 months after the procedure. The patient had the following measurements: height of 175 cm, weight of 66 kg, BMI 21.6, G1, P1. The patient underwent liposuction of the abdomen and waist. A total of 680 ml of fat was removed and 260 ml of purified fat was grafted to each breast. The umbilicus elevation procedure was done at the same time. The shape of the umbilicus was vertical before procedure, yet it became more oval in shape after the procedure. The XU/UP was 19.9/16.2 cm before the procedure, 16.0/18.9 cm at 3 weeks, and 17.0/19.1 cm at 12 months after the procedure. The upper edge of the umbilicus was 3.2 cm below iliac crests (IC) before the procedure, 1.3 cm above the IC at 3 weeks and 0.3 cm above the IC at 12 months. The elevation of the umbilicus was 3.9 cm at 3 weeks, and 2.9 cm at 12 months. The lower abdomen and the periumbilical area became much smoother, without any lumpiness. The scars around the upper portion were from her previous piercings.

Figure 10:
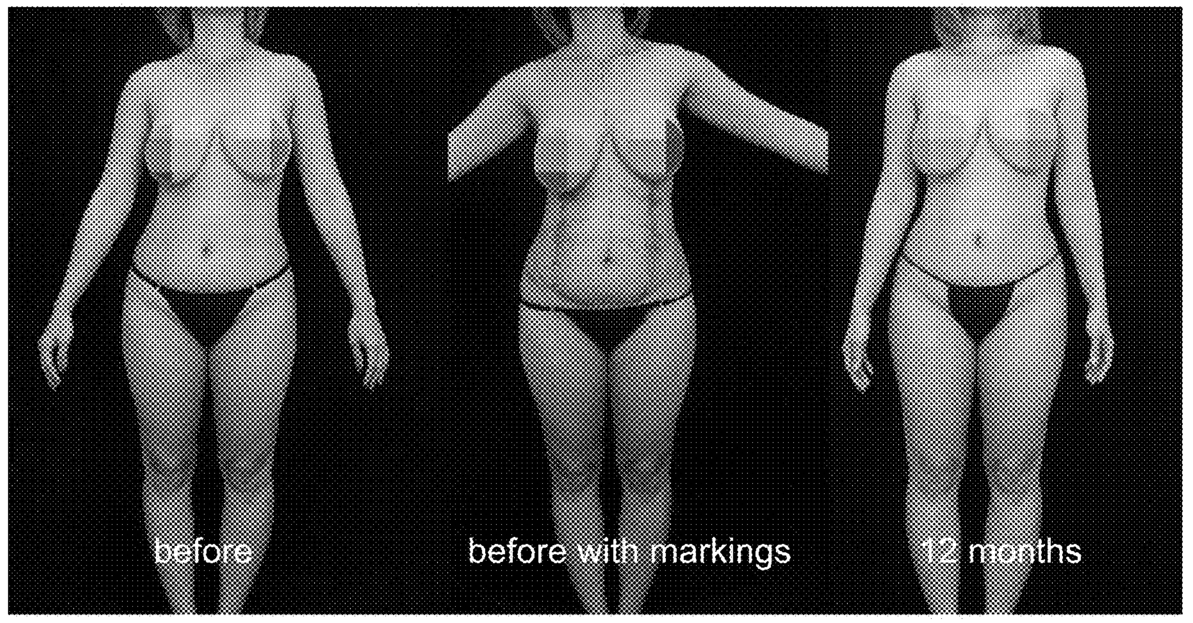
FIG. 10 are images of a patient before and after treatment with an umbilical lift method according to the present disclosure.

FIG. 10 shows images of another patient studied, a 33-year-old female, before the procedure including liposuction and umbilicus lift and 12 months after the procedure. The patient had the following measurements: height of 162 cm, weight of 64 kg, BMI 24.4, G1, P1, and with a history of C-section. The patient underwent liposuction of the abdomen and waist. Areolar lift was also done bilaterally. A total of 980 ml of fat was removed and 320 ml of purified fat was grafted to each breast. The umbilicus elevation procedure was done at the same time. The shape of the umbilicus changed from somewhat round to vertical. The XU/UP was 17.5/12.3 cm before the procedure, and 15.0/14.8 cm at 12 months after procedure. The upper edge of the umbilicus was 3.6 cm below iliac crests (IC) before the procedure and 1.1 cm below the IC at 12 months. The elevation of the umbilicus was 3.2 cm at 3 weeks, and 2.5 cm at 12 months.

Figure 11A:
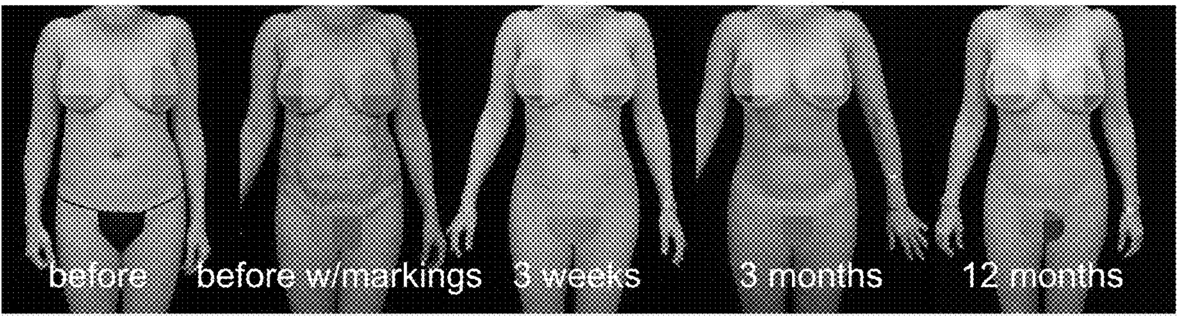
FIGS. 11A and 11B are images of a patient before and after treatment with an umbilical lift method according to the present disclosure.
Figure 11B:
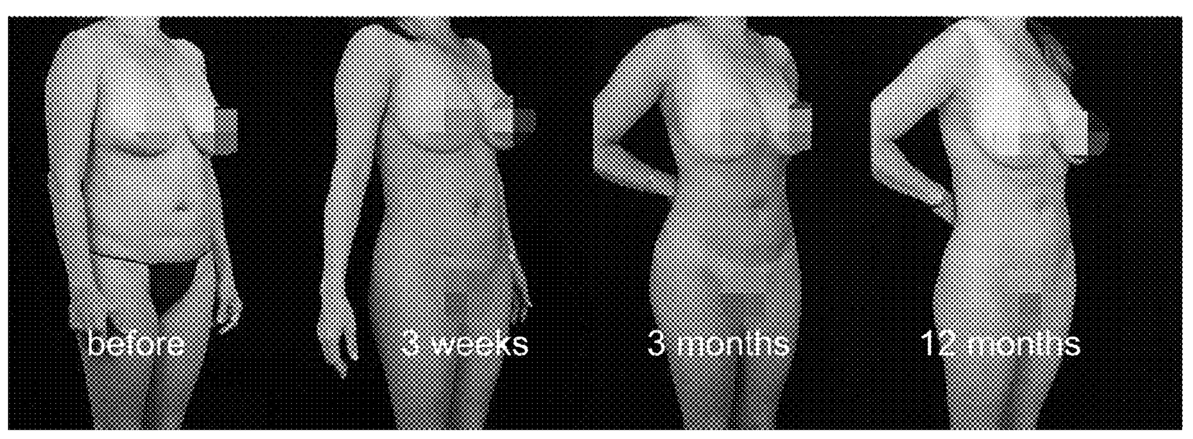

FIGS. 11A and 11B show images of another patient studied, a 47-year-old female, before the procedure including liposuction and umbilicus lift, 3 weeks after the procedure, 3 months after the procedure and 12 months after the procedure. The patient had the following measurements: height of 168 cm, weight of 74 kg, BMI 26.2, G1, P1, with a history of C-section, and unsuccessful liposuction of the abdomen 10 years prior. The patient underwent liposuction of the abdomen, waist accessory breasts, breast tails, waist, and the mons pubis. A total of 1950 ml of fat was removed, and 370 ml of purified fat was grafted to each breast. The patient also had buttock fat grafting with 500 ml to each side. The umbilicus elevation procedure was done at the same time. The shape of the umbilicus changed from horizontal to round. The XU/UP was 17.2/14.3 cm before the procedure, 13.0/18.5 cm at 3 weeks, 14.0/17.5 at 12 months after the procedure. The upper edge of the umbilicus was 1.2 cm below iliac crests (IC) before the procedure, 3.0 cm above the IC and 1.9 cm above the IC at 12 months. The elevation of the umbilicus was 4.2 cm at 3 weeks, and 3.1 cm at 12 months. The dimple-like change above the upper edge of the umbilicus was a result of her previous piercing scar.

Table 1 and FIGS. 8A-11B demonstrate that all patients who underwent abdominal liposuction and the umbilical elevation method using PDO threads had significant improvement in their umbilicus positions. While the mean ratio of XU/UP was 1.29, it became 0.8 at three weeks, and stabilized at 0.98 after 12 months. And this ratio of 0.98 is consistent with the notion that a 1:1 ratio between XU and UP is preferred (see Borille et al. and Craig et al.) given the fact that the new position of the umbilici made the post-liposuction abdomen look more harmonious. The mean UIC (the distance of the upper edge of the umbilicus in reference to the iliac crests was −2.3 (below iliac crests (IC)), 1.4 (above IC), −0.1 cm, before, at 3 weeks and at 12 months, respectively. This number of −0.1 cm is very close to the level of the iliac crests, which again demonstrates that this umbilical elevation procedure with PDO threads successfully restored the youthful umbilical position and helped to beautify the whole abdomen. The mean umbilicus elevation was 3.7 cm at 3 weeks and 2.3 cm at 12 months, respectively. These two numbers demonstrate the powerfulness of the novel PDO thread assisted umbilical elevation procedure. All these numbers were demonstrated to be statistically significant ($p<0.001$). More importantly, the results are permanent because the cogged PDO threads helped to keep the upper abdominal skin in a higher position so that the skin healed in the heightened position after a few months, well before the PDO threads became absorbed (6 to 8 months). As for the cinched upper abdominal skin, it became smoothened after 3 to 5 weeks, probably as a result of the intrinsic property of the skin adapting to the fact that there is no more stretching/pulling force from the weight of the lower abdomen.

Furthermore, umbilicus shapes were improved in most cases (50/52). This effect was even true for those who already had vertically oriented umbilici, as they had their umbilici further improved by making the umbilici more oval/linear. Even the two patients with horizontal-shaped umbilici at the 12-month follow-up had appreciable improvement, as their umbilicus shapes also became somewhat more vertically oriented as compared to before.

Further analysis revealed the additional benefits of the middle and the lower portions of the abdomen becoming tightened. Additionally, lumpy appearances, as a result of skin redundancy, in the lower abdomen, typical of liposuction, were drastically reduced. This phenomenon was a result of the middle and lower abdomen being lifted and lengthened. After a few weeks, the skin healed in a higher position, consequently eliminating the "mommy rolls".

These results of umbilical shape changes and umbilical position lifting are important because they are the type of results that previously could only be achieved by either a tummy tuck surgery or reverse abdominoplasty with conventional techniques.

Comparative Example 2—Only Liposuction Umbilical Lift

Figure 12:
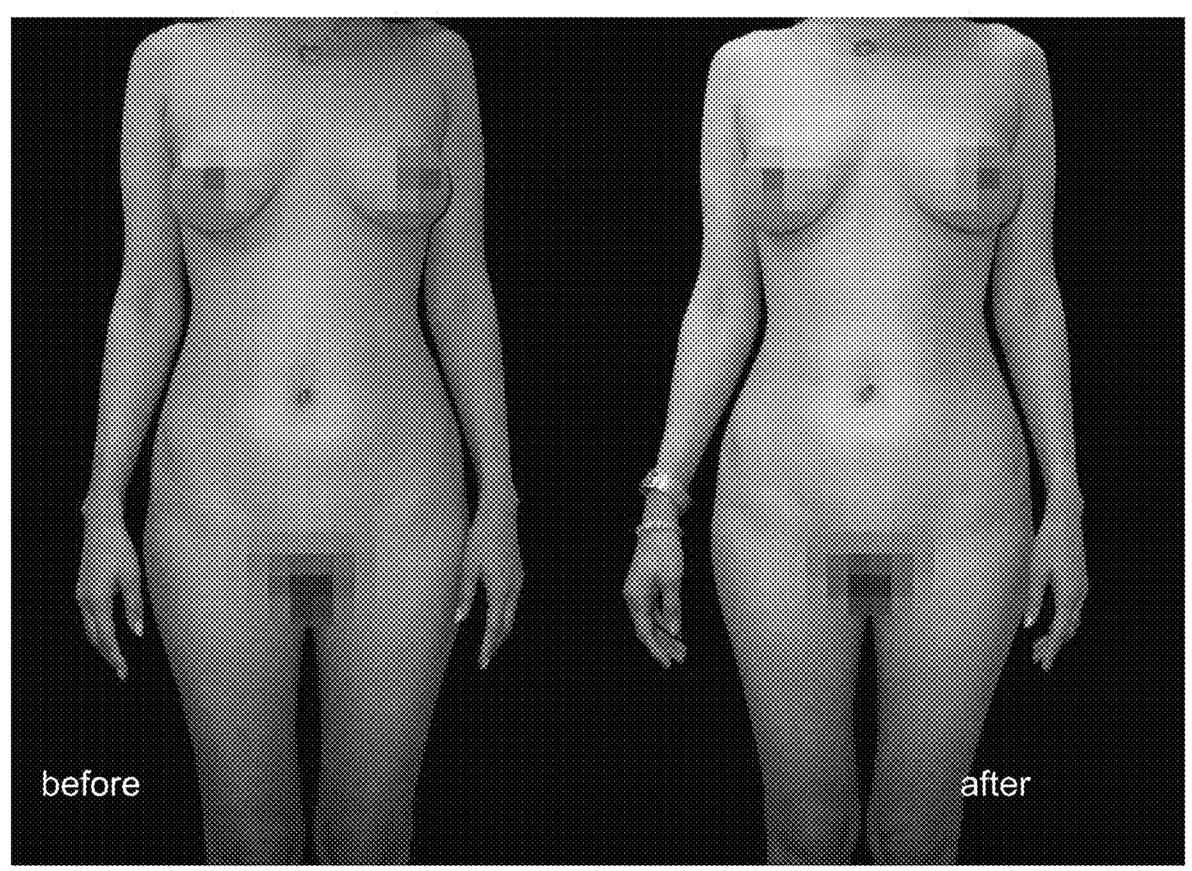
FIG. 12 are images of a patient before and after a comparative liposuction treatment.

Only liposuction was performed on four subjects in an attempt to lift and reshape the patients' umbilicus. FIGS. 12-15 show images of the patients before and after liposuction. FIG. 12 shows before and after images of one patient, a 45-year-old female. The patient had the following measurements: 175 cm height, 66 kg weight, gravida 2, and para 2 (G2, P2). The patient underwent abdominal liposuction with power assisted liposuction (PAL). A total of 600 ml of fat was harvested. Subsequently, 250 ml of fat was grafted into each breast. The after picture was taken 1 year later. The distance from the xiphoid process to the upper edge of the umbilicus (XU) and the distance from the upper edge of the umbilicus to the upper edge of the pubis symphysis (UP) were measured. The XU/UP was 18/16 cm before (left) and 18.5/15.5 cm after (right) the procedure. The upper edge of the umbilicus sits below the iliac crests at 1.5 cm before and 2 cm after the liposuction.

Figure 13:
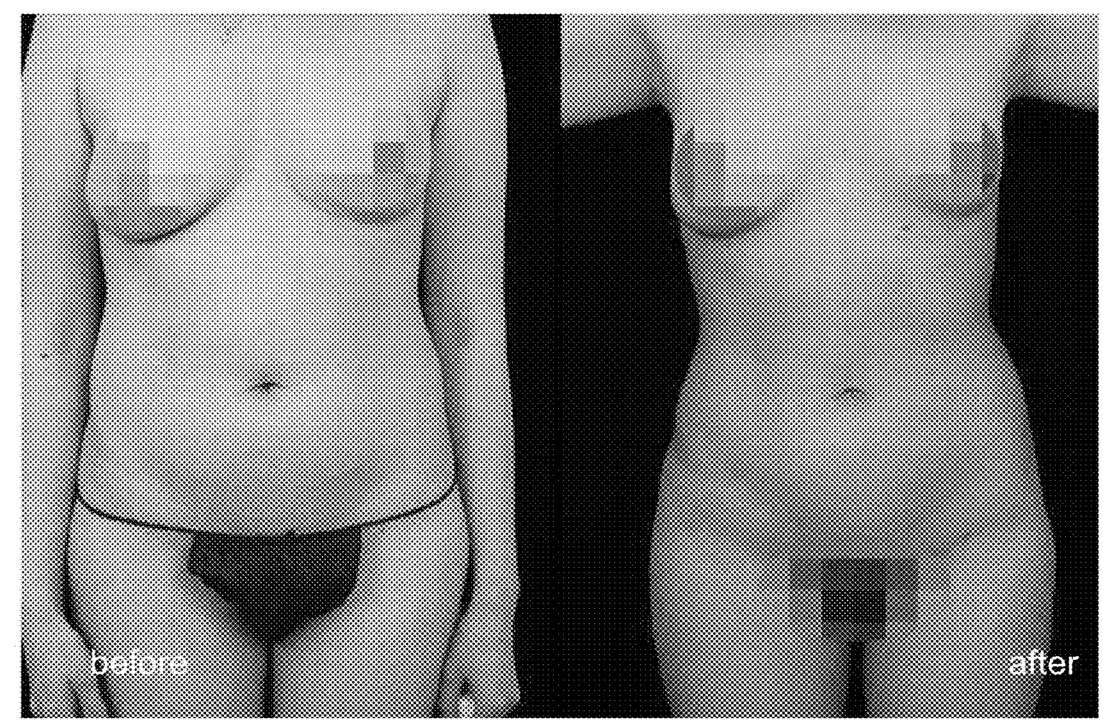
FIG. 13 are images of a patient before and after a comparative liposuction treatment.

FIG. 13 shows before and after images of another patient, a 36-year-old female. The patient had the following measurements: 162 cm height, 59 kg weight, G1, P1. The patient underwent liposuction of the abdomen. A total of 800 ml of fat was removed. The 1-year postop photo shows improvement of her waistline and corset lines. The XU/UP was 16/15 cm before and 17.2/13.8 cm after surgery. The upper edge of the umbilicus sits below the iliac crests at 1.8 cm before and 3 cm after the liposuction.

During the liposuction process, fat from the abdominal wall was removed. This was usually accompanied by the descension and re-draping of the overlying skin onto a lower position, and the umbilicus position simply follows the downward migration (FIGS. 12 and 13). Not surprisingly, the umbilical shape retained its original "sad look" (FIG. 12). In FIG. 12, although the overall shape of the waistline and the corset lines were improved, the lower abdominal "pooch", immediately below the umbilicus, remained, even after liposuction. This "pooch" is a result of excessive skin folding up to form a mound that is mostly composed of skin tissue. Similar umbilicus downward-migration can be seen in FIG. 13.

Figure 14:
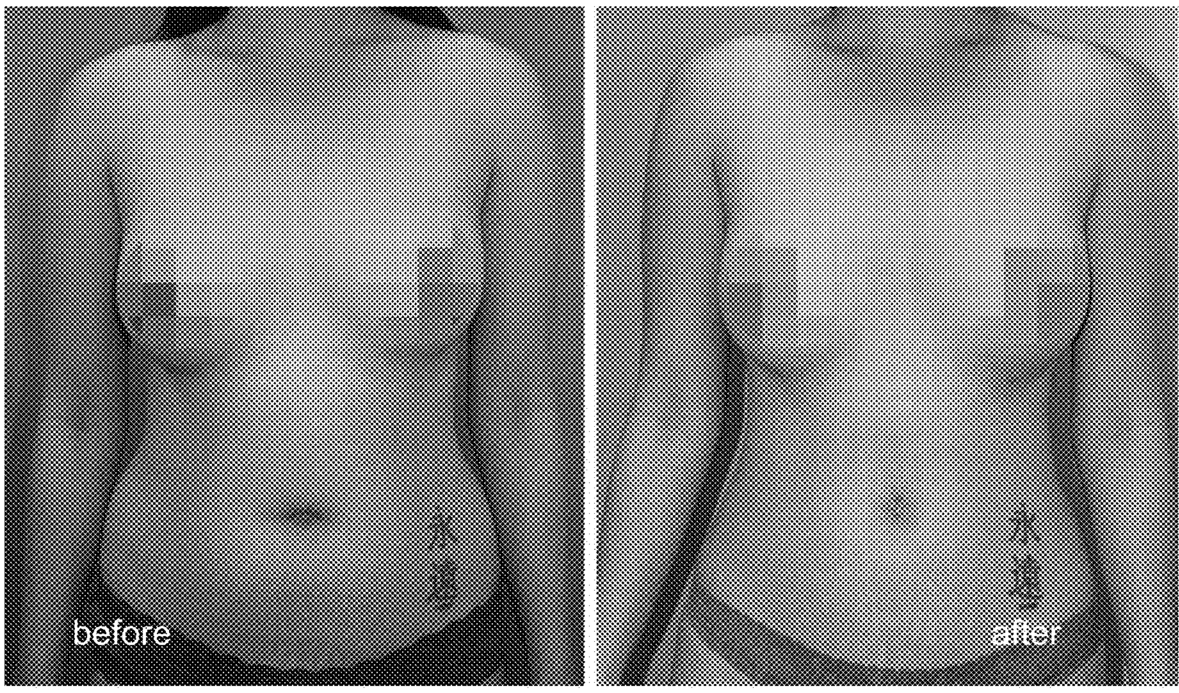
FIG. 14 are images of a patient before and after a comparative liposuction treatment.
Figure 15:
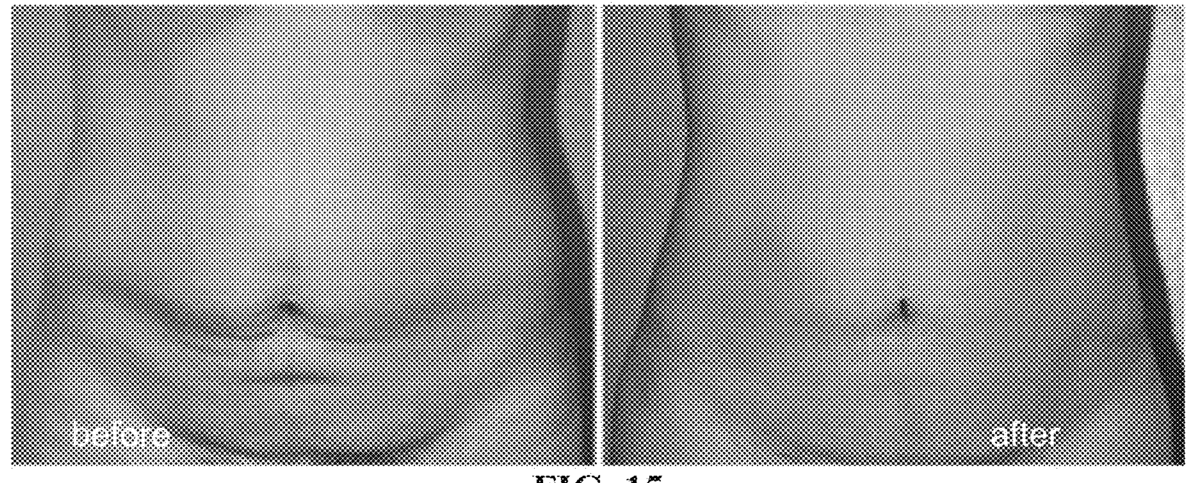
FIG. 15 are images of a patient before and after a comparative liposuction treatment.

FIG. 14 shows before and after images of another patient, a 26-year-old female. The patient had the following measurements: 160 cm height, 65 kg weight, nulliparous, with a history of massive weight loss (40 kg). The patient underwent abdominal and waist liposuction followed by laser lipolysis with a total energy of 40,000 joules for the periumbilical region and the lower abdomen. A total of 1400 ml of fat and oil was removed. 300 ml of purified fat was grafted into each breast. The 1-year post-operation photo shows satisfactory improvement of her waistlines. The XU/UP was 16.5/14.3 cm before and 15.7/15.1 cm after surgery. The upper edge of the umbilicus sits below the iliac crests at 2.1 cm before and 1.3 cm after the liposuction. The scars on the upper pole of the umbilicus were from repeated piercing infections FIG. 15 shows before and after images of another patient, a 46-year-old female. The patient had the following measurements: 164 cm height, 62 kg weight, G2, P2. The patient underwent abdominal liposuction with laser lipolysis. A total of 45,000 joules of energy was delivered, and 200 ml of fat and oil was removed. The 1-year post-operation photo showed improvement of her abdominal topography. The loose skin was tightened. The XU/UP was 16.3/14 cm before and 16/14.3 cm after surgery. The upper edge of the umbilicus sits below the iliac crests for 3.1 cm before and 2.8 cm after the liposuction.

To overcome the problems associated with excess skin after liposuction, laser lipolysis was used to contract the abdominal skin for the patients in FIGS. 14 and 15, which did help to improve the umbilicus position to some extent. However, this improvement was quite limited (FIG. 14, 0.8 cm, and FIG. 15, 0.3 cm), and the shapes resulting from the treatment were not satisfactory. More noticeable was the shape change of the umbilici. In both figures, the loose skin around the umbilicus shrunk significantly, turning transversely oriented umbilici vertical.

Example 3—Liposuction and Breast Lift

Figure 16:
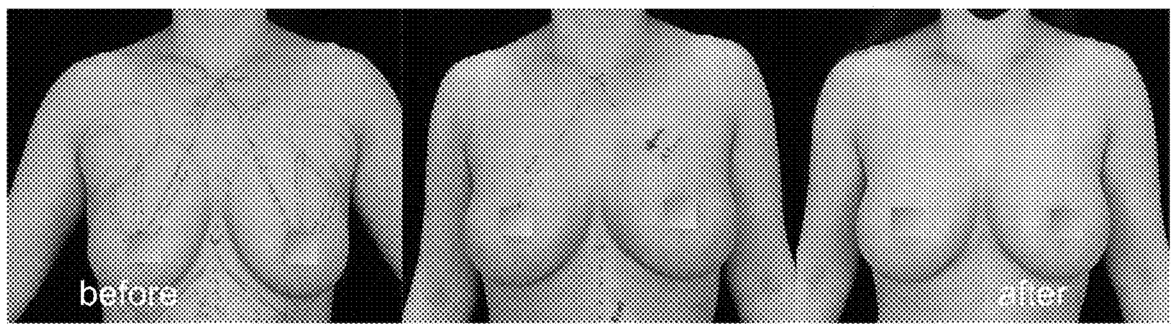
FIG. 16 are images of a patient before and after treatment with a breast lift method according to the present disclosure.

The upper pole and the medial and lateral poles of a breast was liposuctioned from ports made at the two sides of the nipple and one port just above the nipple of a patient. The liposuction was performed in the superficial layer and the layer below the superficial fascia of the breast. A total of about 15 to 50 ml of fat was liposuctioned out and the fat harvested was immediately grafted back to the same liposuctioned area in a layer deeper—close to the breast glandular tissue to keep the breast tissue thickness, while a honey-comb like structure was made to facilitate the breast lift. PDO threads with cogs such as the one described in FIG. 4B were then inserted from the ports made at both sides of the nipple and the port just above the nipple, hugging the upper pole breast skin, at the superficial subcutaneour layer, reaching the upper pole deep ligament layer. After a slight twisting of the cannula that contains the cogged PDO threads, the cannula was retracted, and the cogs were immediately engaged with the surrounding fibrous tissue left from the liposuction. The threads (paired) were left in place after the cannula was removed and then pulled on while pressing on the upper breast skin in order for the cogs to engage more subcutaneous fibrous tissue. Cinching of the skin was achieved by pulling the threads in a caudal direction. The paired threads were then tied and knots were created. After cutting the excess threads at the tail ends, the knots were buried into the ports by the nipple and the nipple-areolar complex was lifted and kept in a lifted position. The lifting effect can be anywhere from 3 cm to 6 cm. For practical purposes, the threads in FIG. 4A can be used as well, just as effective, in combination with the liposuction steps. FIG. 16 shows before and after images of a patient who underwent the above-described breast lift procedure according to the present disclosure.

All publications, patent applications, issued patents and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

What is claimed is:

1. A method of elevating an umbilicus and/or a lower abdomen of a subject, the method comprising:

passing a first end of a first thread through a first path, wherein the first path is defined under the skin of the subject and extends from an upper abdominal region of the subject to an umbilicus region of the subject;

passing a second end of the first thread through a second path, wherein the second path is defined under the skin of the subject and extends from the upper abdominal region of the subject to the umbilicus region of the subject, wherein the first thread comprises a plurality of features;

wherein the first path and the second path are separated by a first lateral distance; and pulling the first end of the first thread, and the second end of the first thread in a direction away from the upper abdominal region to elevate the umbilicus and/or the abdomen.

2. The method of claim 1, wherein the first end of the first thread is introduced through a first entry and passes through the first path to a first exit and the second end of the first thread is introduced through the first entry and passes through the second path to the first exit; or wherein the first end of the first thread is introduced through the first exit and passes through the first path to the first entry and the second end of the first thread is introduced through the first exit and passes through the second path to the first entry.

3. The method of claim 2, wherein a distance between the first entry and the first exit is smaller after pulling of the first end of the first thread and the second end of the first thread compared to a distance between the first entry and the first exit prior to pulling.

4. The method of claim 2, further comprising:

passing a first end of a second thread through the first path, passing a second end of the second thread through the second path; and pulling the first end of the second thread, and the second end of the second thread in the direction away from the upper abdominal region to elevate the umbilicus and/or the abdomen;

wherein the second thread comprises a plurality of features.

5. The method of claim 4, wherein the first end of the second thread is introduced through the first entry and passes through the first path to the first exit and the second end of the second thread is introduced through the first entry and passes through the second path to the first exit or wherein the first end of the second thread is introduced through the first exit and passes through the first path to the first entry and the second end of the second thread is introduced through the first exit and passes through the second path to the first entry.

6. The method of claim 4, further comprising:

passing at least one of a third thread, a fourth thread, a fifth thread, a sixth thread, a seventh thread, an eighth thread, a ninth thread, and a tenth thread as follows:

(i) a first end of a third thread through the first path and a second end of the third thread through the second path;

(ii) a first end of a fourth thread through the first path and a second end of the fourth thread through the second path;

(iii) a first end of a fifth thread through the first path and a second end of the fifth thread through the second path;

(iv) a first end of a sixth thread through the first path and a second end of the sixth thread through the second path;

(v) a first end of a seventh thread through the first path and a second end of the seventh thread through the second path;

(vi) a first end of an eighth thread through the first path and a second end of the eighth thread through the second path;

(vii) a first end of a ninth thread through the first path and a second end of the ninth thread through the second path; and (viii) a first end of a tenth thread through the first path and a second end of the tenth thread through the second path;

pulling, in the direction away from the upper abdominal region to elevate the umbilicus and/or the abdomen, one or more of:

(i) the first end of the third thread and the second end of the third thread, when present;

(ii) the first end of the fourth thread and the second end of the fourth thread, when present;

(iii) the first end of the fifth thread and the second end of the fifth thread, when present;

(iv) the first end of the sixth thread and the second end of the sixth thread, when present;

(v) the first end of the seventh thread and the second end of the seventh thread, when present;

(vi) the first end of the eighth thread and the second end of the eighth thread, when present;

(vii) the first end of the ninth thread and the second end of the ninth thread, when present;

and (viii) the first end of the tenth thread, and the second end of the tenth thread, when present;

wherein one or more of the third thread, the fourth thread, the fifth thread, the sixth thread, the seventh thread, the eighth thread, the ninth thread, and the tenth thread each comprises a plurality of features.

7. The method of claim 4, further comprising fastening the first end of the second thread, the second end of the second thread, or both.

8. The method of claim 4, wherein the first end of the first thread and the second end of the first thread are not fastened and/or the first end of the second thread and the second end of the second thread are not fastened.

9. The method of claim 4, wherein the first thread and the second thread each have a length of about 5 cm to about 120 cm and/or the first thread and the second thread each have a size according to the United States Pharmacopeia (USP) system of about 6-0 to about 4.

10. The method of claim 4, wherein the first thread and the second thread independently are a unitary thread or a divided thread and/or the first thread and the second thread each are introduced through a cannula or a needle.

11. The method of claim 4, wherein the first thread and the second thread each comprise a material selected from the group consisting of polydioxanone (PDO), polyglactin, poliglecaprone, polycaprolactone (PCL), poly-L-lactic acid, polypropylene, polypropylene, nylon, silk, cotton, polyester, catgut, metal wire, collagen fiber, a tendinous material from a heterologous donor or animal, autologous tissue, and a combination thereof and/or the first thread and the second thread are each selected from the group consisting of a mesh, a cord, a ribbon, a net, a sheet, or a combination thereof.

12. The method of claim 2, further comprising:

passing a first end of a second thread through a third path, wherein the third path is defined under the skin of the subject and extends from the upper abdominal region of the subject to the umbilicus region of the subject;

passing a second end of the second thread through a fourth path, wherein the fourth path is defined under the skin of the subject and extends from the upper abdominal region of the subject to the umbilicus region of the subject;

wherein the third path and the fourth path are separated by a second lateral distance;

and pulling the first end of the second thread, and the second end of the second thread in the direction away from the upper abdominal region to elevate the umbilicus and/or the abdomen.

13. The method of claim 12, wherein the first end of the second thread is introduced through the first entry and passes through the third path to the first exit and the second end of the second thread is introduced through the first entry and passes through the fourth path to the first exit, or wherein the first end of the second thread is introduced through the first exit and passes through the third path to the first entry and the second end of the second thread is introduced through the first exit and passes through the fourth path to the first entry.

14. The method of claim 12, wherein the second lateral distance is greater than the first lateral distance.

15. The method of claim 2, wherein the first entry comprises a plurality of discrete entry points and/or wherein the first exit comprises a plurality of discrete exit points.

16. The method of claim 1, further comprising fastening the first end of the first thread, the second end of the first thread, or both.

17. The method of claim 1, wherein one or more of the following are satisfied:

(i) the plurality of features engage tissue under the skin of the subject upon pulling of the first thread and the second thread;

(ii) the plurality of features is one-directional, bi-directional, or multi-directional; and (iii) the plurality of features is selected from the group consisting of barbs, knots, cones, beads, cogs, or a combination thereof.

18. The method of claim 1, further comprising the subject undergoing liposuction in the abdominal region or other regions of the subject prior to the passing of the first end of the first thread through the first path and passing the second end of the first thread through the second path.

* * * * *